US012728084B2

(12) United States Patent
Gillant et al.

(10) Patent No.: US 12,728,084 B2
(45) Date of Patent: Sep. 8, 2026

(54) COSMETIC OR DERMATOLOGICAL COMPOSITION COMPRISING A MEROCYANINE AND A GAMMA-BUTYROLACTONE AND/OR A GAMMA-BUTYROLACTAM

(71) Applicant: L'OREAL, Paris (FR)

(72) Inventors: Flavie Gillant, Chevilly la Rue (FR); Xavier Marat, Aulnay-sous-Bois (FR); Eva Muller, Ortenburg-Dorfbach (DE); Angélina Roudot, Chevilly la Rue (FR); Didier Candau, Chevilly la Rue (FR)

(73) Assignee: L'OREAL, Paris (FR)

( * ) Notice: Subject to any disclaimer, the term of this patent is extended or adjusted under 35 U.S.C. 154(b) by 178 days.

(21) Appl. No.: 18/705,249

(22) PCT Filed: Dec. 12, 2022

(86) PCT No.: PCT/EP2022/085433

§ 371 (c)(1),
(2) Date: Apr. 26, 2024

(87) PCT Pub. No.: WO2023/110767

PCT Pub. Date: Jun. 22, 2023

(65) Prior Publication Data

US 2025/0235392 A1 Jul. 24, 2025

(30) Foreign Application Priority Data

Dec. 17, 2021 (FR) ........................................ 2113849
Oct. 20, 2022 (FR) ........................................ 2210879

(51) Int. Cl.

| | |
|---|---|
| ***A61K 8/41*** | (2006.01) |
| ***A61Q 17/04*** | (2006.01) |
| ***C07C 253/32*** | (2006.01) |

(52) U.S. Cl.

CPC ................ *A61K 8/41* (2013.01); *A61Q 17/04* (2013.01); *C07C 253/32* (2013.01); *A61K 2800/5922* (2013.01)

(58) Field of Classification Search

None

See application file for complete search history.

(56) References Cited

U.S. PATENT DOCUMENTS

| | | | |
|---|---|---|---|
| 2,757,125 | A * | 7/1956 | Mudrak |
| 8,454,940 | B2 | 6/2013 | Wagner et al. |
| 2010/0183529 | A1 * | 7/2010 | Richard et al. |
| 2014/0294743 | A1 | 10/2014 | Richard et al. |
| 2020/0281829 | A1 | 9/2020 | Guiramand et al. |

FOREIGN PATENT DOCUMENTS

| | | | |
|---|---|---|---|
| WO | WO 2019002495 | * | 1/2019 |
| WO | 2020002537 | A1 | 1/2020 |

OTHER PUBLICATIONS

International Search Report and Written Opinion issued Mar. 27, 2023 for corresponding PCT Application No. PCT/EP2022/085433.

* cited by examiner

*Primary Examiner* — Robert A Wax
(74) *Attorney, Agent, or Firm* — POLSINELLI PC

(57) ABSTRACT

The present invention relates to a composition, in particular a cosmetic or dermatological composition, comprising:

a) at least one merocyanine corresponding to formula (3) below, and also the geometric isomer forms, notably the E/E- or E/Z-geometric isomer forms, thereof:

[formula 3]

in which:

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, it being possible for said groups to be interrupted by one or more O; and b) at least one compound chosen from suitably selected gamma-butyrolactones and gamma-butyrolactams.

The present invention also relates to a non-therapeutic cosmetic method for caring for and/or making up a keratin material, comprising the application, to the surface of said keratin material, of at least one composition as defined above.

23 Claims, No Drawings

COSMETIC OR DERMATOLOGICAL COMPOSITION COMPRISING A MEROCYANINE AND A GAMMA-BUTYROLACTONE AND/OR A GAMMA-BUTYROLACTAM

CROSS-REFERENCE TO RELATED APPLICATIONS

This application is a national stage application (under 35 U.S.C. § 371) of PCT/EP2022/085433, filed Dec. 12, 2022, which in turn claims priority to French Application No. 2113849, filed Dec. 17, 2021, and French Application No. 2210879, filed Oct. 20, 2022, which are incorporated herein by reference in their entireties.

The present invention relates to a cosmetic or dermatological composition, comprising at least one merocyanine of formula (3) which will be defined below in detail and at least one compound chosen from suitably selected gamma-butyrolactones and gamma-butyrolactams.

The present invention also relates to a non-therapeutic cosmetic method for caring for and/or making up a keratin material, comprising the application, to the surface of said keratin material, of at least one composition according to the invention as defined above.

The present invention also relates to a non-therapeutic cosmetic method for limiting the darkening of the skin and/or improving the colour and/or the uniformity of the complexion, comprising the application, to the surface of the keratin material, of at least one composition as defined previously.

The present invention also relates to a non-therapeutic cosmetic method for preventing and/or treating the signs of ageing of a keratin material, comprising the application, to the surface of the keratin material, of at least one composition as defined previously.

It is known that radiation with a wavelength of between 280 nm and 400 nm enables tanning of the human epidermis and that radiation with a wavelength of between 280 and 320 nm, known under the name UVB rays, harms the development of a natural tan. Exposure is also liable to bring about a detrimental change in the biomechanical properties of the epidermis, which is reflected by the appearance of wrinkles, leading to premature ageing of the skin.

It is also known that UVA rays with a wavelength of between 320 and 400 nm penetrate more deeply into the skin than UVB rays. UVA rays cause immediate and persistent tanning of the skin. Daily exposure to UVA rays, even of short duration, under normal conditions can result in damage to the collagen fibres and the elastin, which is reflected by a modification of the microrelief of the skin, the appearance of wrinkles and uneven pigmentation (liver spots, heterogeneity of the complexion).

Protection against UVA and UVB radiation is thus necessary. An effective photoprotective product must protect against both UVA and UVB radiation.

Many photoprotective compositions have been proposed to date to overcome the effects induced by UVA and/or UVB radiation. They generally contain organic UV-screening agents and/or inorganic UV-screening agents, which function according to their own chemical nature and according to their own properties by absorption, reflection or scattering of the UV radiation. They generally contain mixtures of fat-soluble organic screening agents and/or of water-soluble UV-screening agents combined with metal oxide pigments, such as titanium dioxide or zinc oxide.

Many cosmetic compositions intended to limit darkening of the skin, and to improve the colour and uniformity of the complexion have been proposed to date. It is well known in the field of antisun products that such compositions can be obtained by using UV-screening agents, and in particular UVB-screening agents. Some compositions can also contain UVA-screening agents. This screening system must cover UVB protection, for the purpose of limiting and controlling the neosynthesis of melanin promoting overall pigmentation, but must also cover UVA protection, in order to limit and control the oxidation of the pre-existing melanin resulting in the darkening of the colour of the skin.

However, it is extremely difficult to find a composition containing a particular combination of UV-screening agents that would be specially suitable for photoprotection of the skin and particularly for an improvement in the quality of the skin both in terms of the colour and in terms of its mechanical elasticity properties.

Advantageously, this improvement is particularly desired on skin which is already pigmented, for the purpose of not enhancing either the pigmentary melanin load or the structure of the melanin already present within the skin.

In fact, the majority of organic UV-screening agents are constituted of aromatic compounds which absorb in the range of wavelengths between 280 and 370 nm. In addition to their solar radiation-screening capacity, the desired photoprotective compounds must also have good cosmetic properties, good solubility in the usual solvents and in particular in fatty substances such as oils, or in water, and also good photostability alone or in combination with other UV-screening agents. They must also be colourless or at least have a colour that is cosmetically acceptable for consumers.

One of the main disadvantages known to date of these compositions is that these screening systems have insufficient effectiveness against UV radiation and particularly against long UVA radiation with wavelengths above 370 nm with the aim of controlling light-induced pigmentation and the development thereof by a system which screens out UV radiation over the whole of the UV spectrum.

Among all the compounds that have been recommended for this purpose, an advantageous family of UV-screening agents which is constituted of carbonated merocyanine derivatives has been proposed, which is described in U.S. Pat. No. 4,195,999, application WO 2004/006878 and document IP COM Journal 4 (4), 16 No. IPCOM000011179D published on Apr. 3, 2004. These compounds exhibit very good screening properties in the long UVA radiation range but exhibit a solubility in the usual solvents, both in the aqueous phase and in the fatty phase, which is only slightly satisfactory and a photostability which is unsatisfactory for some merocyanines.

With the aim of searching for other merocyanines which have better solubility in the usual solvents and better photostability, application WO 2013/011094 has proposed merocyanines comprising polar groups constituted of hydroxyl and ether functions, which show good long UVA-screening efficiency. However, the solubility of these particular merocyanines is still not entirely satisfactory and often requires a tedious formulating process. Moreover, the large amounts of solvent necessary in order to solubilize this type of merocyanine can result in cosmetic unpleasantness, such as a tacky and greasy effect on application.

There thus remains the need to improve the solubility of these merocyanines in cosmetic compositions, in particular photoprotective formulations, both in the aqueous phase and in the fatty phase, while still obtaining good cosmeticity.

The applicant has surprisingly discovered that by using a gamma-butyrolactone derivative such as for example gamma-valerolactone or a gamma-butyrolactam derivative such as for example 2-pyrrolidone, 1,3-dimethylbutyl 1-butyl-5-oxopyrrolidine-3-carboxylate, 2-pyrrolidone-5-carboxylic acid, and tert-butyl (S)-2-pyrrolidone-5-carboxylate, it is possible to substantially improve the solubility of these merocyanines both in an aqueous phase and in a fatty phase. This discovery forms the basis of the present invention.

Thus, in accordance with one of the subjects of the present invention, there is now provided a cosmetic or dermatological composition comprising at least one merocyanine of formula (3) and at least one gamma-butyrolactone derivative and/or one gamma-butyrolactam derivative which will be defined below in detail.

Moreover, there also remains the need to improve the solubility of merocyanines in the presence of organic screening agents. Indeed, the addition of additional screening agents can destabilize compositions comprising a merocyanine.

The applicant has surprisingly discovered that by using a gamma-butyrolactone derivative such as for example gamma-valerolactone or a gamma-butyrolactam derivative such as for example 2-pyrrolidone, 1,3-dimethylbutyl 1-butyl-5-oxopyrrolidine-3-carboxylate, 2-pyrrolidone-5-carboxylic acid (PCA), tert-butyl (S)-2-pyrrolidone-5-carboxylate (PCA ester) and 1-butyl-5-oxopyrrolidone-3-carboxylic acid, it is possible to substantially improve the solubility of these merocyanines in an aqueous phase or in a fatty phase, even in the presence of additional organic UV-screening agents.

The applicant has also discovered that the use of a gamma-butyrolactone derivative such as for example gamma-valerolactone or a gamma-butyrolactam derivative such as for example 2-pyrrolidone, 1,3-dimethylbutyl 1-butyl-5-oxopyrrolidine-3-carboxylate, 2-pyrrolidone-5-carboxylic acid (PCA), tert-butyl (S)-2-pyrrolidone-5-carboxylate (PCA ester) and 1-butyl-5-oxopyrrolidone-3-carboxylic acid makes it possible to obtain good cosmeticity of the composition comprising the merocyanines, said composition being in particular non-greasy and non-tacky.

The present invention also relates to a non-therapeutic cosmetic method for caring for and/or making up a keratin material, comprising the application, to the surface of said keratin material, of at least one composition according to the invention as defined above.

The present invention also relates to a non-therapeutic cosmetic method for limiting the darkening of the skin and/or improving the colour and/or the uniformity of the complexion, comprising the application, to the surface of the keratin material, of at least one composition as defined previously.

The present invention also relates to a non-therapeutic cosmetic method for preventing and/or treating the signs of ageing of a keratin material, comprising the application, to the surface of the keratin material, of at least one composition as defined previously.

The present invention also relates to the use of a gamma-butyrolactone derivative such as for example gamma-valerolactone or of a gamma-butyrolactam derivative such as for example 2-pyrrolidone, 1,3-dimethylbutyl 1-butyl-5-oxopyrrolidine-3-carboxylate, 2-pyrrolidone-5-carboxylic acid (PCA), tert-butyl (S)-2-pyrrolidone-5-carboxylate (PCA ester) and 1-butyl-5-oxopyrrolidone-3-carboxylic acid for solubilizing a merocyanine of formula (3) as defined below, notably for solubilizing these molecules in the fatty phase and/or in the aqueous phase.

Other features, aspects and advantages of the invention will become apparent on reading the detailed description which follows.

The composition according to the invention is intended for topical application and thus contains a physiologically acceptable medium. The term "physiologically acceptable medium" means here a medium that is compatible with keratin materials.

In the context of the present invention, the term "keratin material" is understood to mean in particular the skin, scalp, keratin fibres, such as the eyelashes, eyebrows, head hair and body hair, nails, mucous membranes, such as the lips, and more particularly the skin and mucous membranes (body, face, area around the eyes, eyelids, lips, preferably body, face and lips).

In the text hereinbelow, unless otherwise indicated, the limits of a range of values are included in that range, notably in the expressions "between" and "ranging from . . . to . . . ".

Moreover, the expressions "at least one" and "at least" used in the present description are equivalent respectively to the expressions "one or more" and "greater than or equal to".

According to the invention, the term "preventing" or "prevention" is intended to mean reducing the risk of occurrence or slowing down the occurrence of a given phenomenon, namely, according to the present invention, the signs of ageing of a keratin material.

Merocyanines

According to the present invention, use will be made of a family of merocyanines corresponding to formula (3) below, and also the geometric isomer forms, notably the E/E- or E/Z-geometric isomer forms, thereof:

[Formula 3]

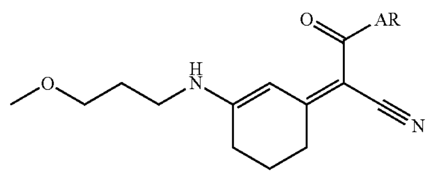

in which:

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, it being possible for said groups to be interrupted by one or more O.

The merocyanine compounds of the invention may be in the E/E- or E/Z-geometric isomer forms thereof:

[formula 3]

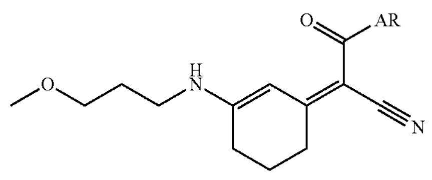

-continued

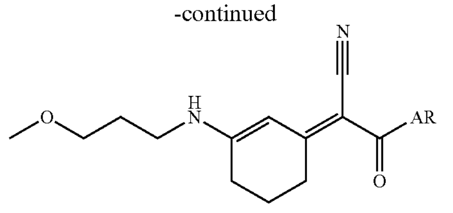

The compounds of formula (3) which are even more preferential are those where:

A is —O—; R is a $C_1$-$C_{22}$ alkyl, which can be interrupted by one or more O.

Use will more particularly be made, among the compounds of formula (3), of those chosen from the following group and also the geometric isomer forms, notably the E/E- or E/Z-geometric isomer forms, thereof:

TABLE 1

| | |
|---|---|
| 14 | 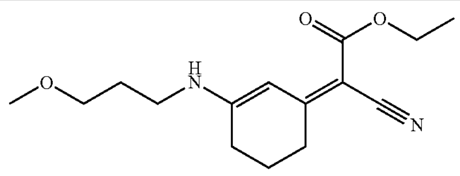 [SMILES: CCOC(=O)/C(C#N)=C1\C=C(NCCCOC)CCC1]<br>ethyl (2Z)-cyano{3-[(3-methoxypropyl)amino]cyclohex-2-en-1-ylidene}ethanoate |
| 15 | 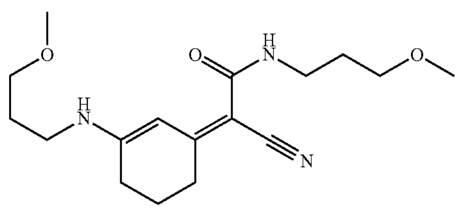 [SMILES: COCCCNC(=O)/C(C#N)=C1\C=C(NCCCOC)CCC1]<br>(2Z)-2-cyano-N-(3-methoxypropyl)-2-{3-[(3-methoxypropyl)amino]cyclohex-2-en-1-ylidene}ethanamide |
| 25 | 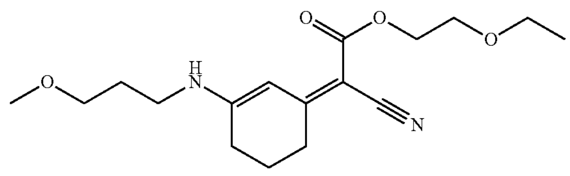 [SMILES: CCOCCOC(=O)/C(C#N)=C1\C=C(NCCCOC)CCC1]<br>2-ethoxyethyl (2Z)-cyano{3-[(3-methoxypropyl)amino]cyclohex-2-en-1-ylidene}ethanoate |
| 27 | 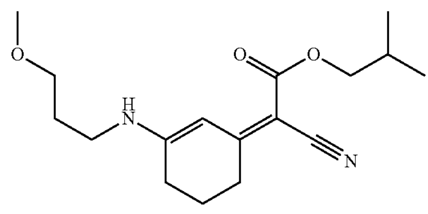 [SMILES: COCCCNC1=C/C(=C(/C#N)C(=O)OCC(C)C)CCC1]<br>2-methylpropyl (2Z)-cyano{3-[(3-methoxypropyl)amino]cyclohex-2-en-1-ylidene}ethanoate |
| 29 | 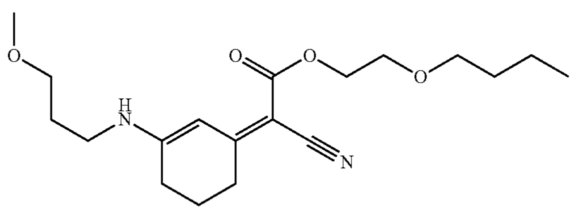 [SMILES: CCCCOCCOC(=O)/C(C#N)=C1\C=C(NCCCOC)CCC1]<br>2-butoxyethyl (2Z)-cyano{3-[(3-methoxypropyl)amino]cyclohex-2-en-1-ylidene}ethanoate |

TABLE 1-continued

31

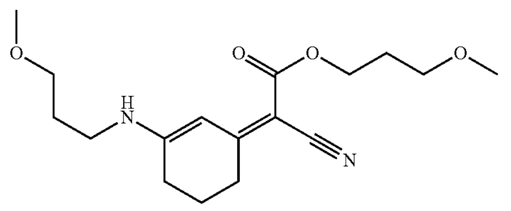 [SMILES: COCCCNC1=C/C(=C(/C#N)C(=O)OCCCOC)CCC1]

3-methoxypropyl (2Z)-cyano{3-[(3-methoxypropyl)amino]cyclohex-2-en-1-ylidene}ethanoate

37

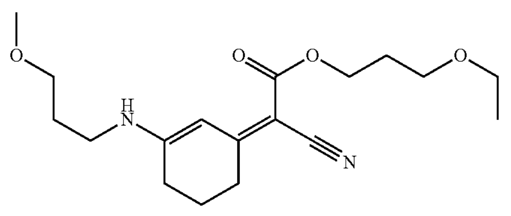 [SMILES: CCOCCCOC(=O)/C(C#N)=C1\C=C(NCCCOC)CCC1]

3-ethoxypropyl (2Z)-cyano{3-[(3-methoxypropyl)amino]cyclohex-2-en-1-ylidene}ethanoate.

According to a more particularly preferred embodiment of the invention, use will be made of the compound 2-ethoxyethyl (2Z)-cyano{3-[(3-methoxypropyl)amino]cyclohex-2-en-1-ylidene}ethanoate (25) in its E/E- and/or E/Z-geometric configuration.

The E/Z form has the following structure:

[formula 25]

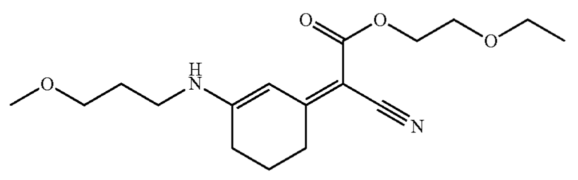

The E/E form has the following structure:

[formula 25a]

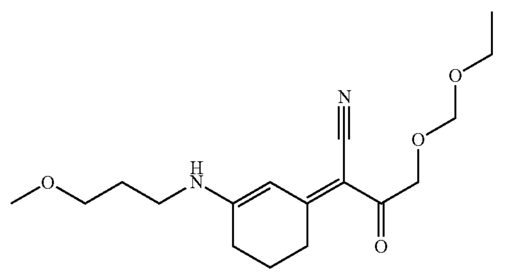

The screening merocyanines in accordance with the invention may be present in the compositions according to the invention in a concentration ranging from 0.1% to 15% by weight, and preferentially from 0.2% to 10% by weight and even better still from 0.5% to 5% by weight relative to the total weight of the composition.

The compounds of formula (3), which form a carbocyclic ring containing 6 carbon atoms, may be prepared according to the protocols described in patent application WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 on col. 13, line 66-col. 14, line 57, and the references cited in this regard.

In particular, the compounds of formula (3), such as the compound 2-ethoxyethyl (2Z)-cyano{3-[(3-methoxypropyl)amino]cyclohex-2-en-1-ylidene}ethanoate (25) can be synthesized according to the synthesis scheme described in the publication by B. Winkler et al., Tetrahedron Letters, 55 (2014) 1749-1751, which is entitled "A cyclic merocyanine UV-A absorber: mechanism of formation and crystal structure", and represented below, for the compounds of formula (3):

[formula 4]

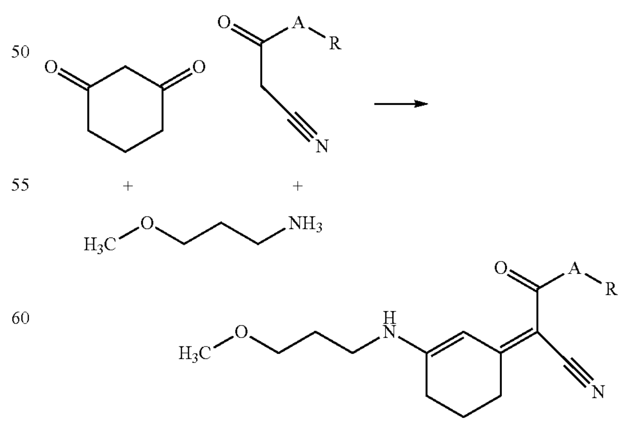

and more particularly for compound 25 described in table 1:

[formula 5]

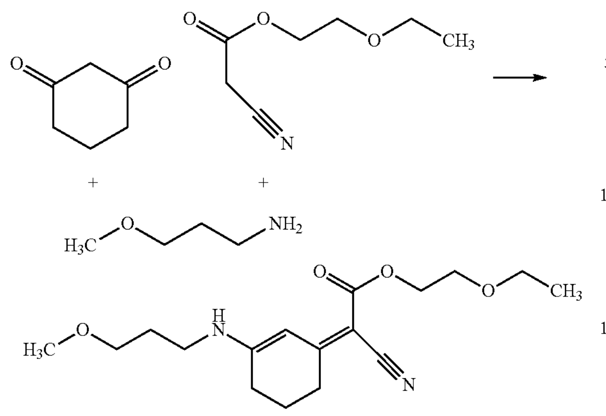

Gamma-Butyrolactones and/or Gamma-Butyrolactams

Composition in accordance with the invention comprises at least one compound chosen from gamma-butyrolactones and gamma-butyrolactams corresponding to the formula defined below, and also the organic or mineral acid or base salts thereof, or the solvates thereof such as hydrates:

[formula 38]

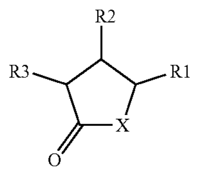

in which:

X represents an oxygen atom or a nitrogen atom bearing an R4 radical, with R4 representing a hydrogen atom or a linear or branched $C_1$-$C_6$ alkyl radical, R1, R2 and R3 represent, independently of one another:
- a hydrogen atom,
- a linear or branched $C_1$-$C_6$ alkyl radical, or
- an —$[O]_n$—C(O)—$[O]_p$—R5 radical, where:
  - n is equal to 0 or 1, p is equal to 0 or 1, with n+p equal to 1 or 2,
  - R5 represents a hydrogen atom or a linear or branched $C_1$-$C_6$ alkyl radical.

According to a particular embodiment of the invention, X represents an oxygen atom.

According to a particular embodiment of the invention, X represents an oxygen atom or a nitrogen atom bearing an R4 radical, with R4 representing a hydrogen atom or a linear or branched $C_1$-$C_6$ alkyl radical, preferably a hydrogen atom or a linear or branched $C_1$-$C_4$ alkyl radical, and even more preferentially a hydrogen atom or a linear $C_1$-$C_4$ alkyl radical.

According to a particular embodiment of the invention, R1, R2 and R3 represent, independently of one another:
- a hydrogen atom,
- a linear or branched $C_1$-$C_6$, preferably $C_1$-$C_4$, alkyl radical, or
- an —$[O]_n$—C(O)—$[O]_p$—R5 radical, where:
  - n is equal to 0 or 1, p is equal to 0 or 1, with n+p equal to 1,
  - R5 represents a hydrogen atom or a linear or branched $C_1$-$C_6$ alkyl radical.

According to a preferred embodiment, n=0 and p=1.

According to a preferred embodiment of the invention, R4 represents a hydrogen atom or a linear or branched $C_1$-$C_4$ alkyl radical, such as for example a methyl, ethyl, n-propyl, isopropyl, tert-butyl, isobutyl or n-butyl radical, preferably a linear $C_1$-$C_4$ alkyl radical, such as for example an n-butyl radical.

According to a preferred embodiment, R5 represents a hydrogen atom or a branched $C_1$-$C_6$ alkyl radical, for example a tert-butyl radical or a 1,3-dimethylbutyl radical.

According to another preferred embodiment, R5 represents a branched $C_1$-$C_6$ alkyl radical, preferably a tert-butyl radical.

The acceptable salts of the compounds of formula 38 include conventional non-toxic salts of said compounds, such as those formed from organic or inorganic acids. Examples that may be mentioned include the salts of mineral acids, such as sulfuric acid, hydrochloric acid, hydrobromic acid or phosphoric acid. Mention may also be made of the salts of organic acids, which may include one or more carboxylic, sulfonic or phosphonic acid groups. They may be linear, branched or cyclic aliphatic acids, or alternatively aromatic acids. These acids may also include one or more heteroatoms chosen from O and N, for example in the form of hydroxyl groups. Mention may notably be made of propionic acid, acetic acid, terephthalic acid, citric acid, tartaric acid and lactic acid.

The salts of organic or mineral bases such as the ammonium salts, the alkanolamine salts such as those of triethanolamine or of aminopropanediol, and the salts of alkali metals or alkaline-earth metals such as sodium, potassium, calcium or magnesium.

The preferred salts are those obtained from hydrochloric acid, sulfuric acid, acetic acid, tartaric acid, citric acid and lactic acid and also the salts of alkali metals such as sodium, potassium or calcium.

According to a particular embodiment of the invention, the composition comprises at least one compound chosen from those which are defined below, and also the organic or mineral acid or base salts thereof, or the solvates thereof such as hydrates, and optionally the optical isomers, stereoisomers, enantiomers and diastereoisomers thereof and geometric isomers thereof:

gamma-valerolactone of the following formula:

[formula 39]

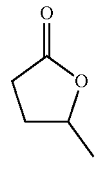

2-pyrrolidone of the following formula:

[formula 40]

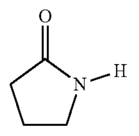

1,3-dimethylbutyl 1-butyl-5-oxopyrrolidine-3-carboxylate of the following formula:

[formula 41]

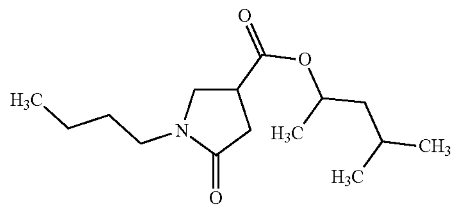

2-pyrrolidone-5-carboxylic acid (PCA) of the following formula:

[formula 42]

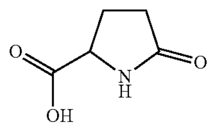

tert-butyl (S)-2-pyrrolidone-5-carboxylate (PCA ester) of the following formula:

[formula 43]

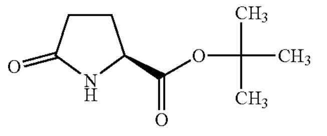

1-butyl-5-oxopyrrolidone-3-carboxylic acid of the following formula:

[formula 43a]

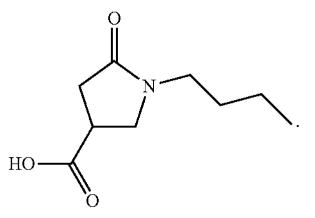

According to a particular embodiment of the invention, the composition comprises at least one gamma-butyrolactone, preferably a gamma-butyrolactone of formula 38 as defined above in which X is an oxygen atom.

According to another particular embodiment of the invention, the composition comprises at least one gamma-butyrolactam, preferably a gamma-butyrolactam of formula 38 as defined above in which X is a nitrogen atom bearing an R4 radical.

The compounds of formula 38 may be obtained according to the syntheses as described in patent application FR 2 968 547.

In particular, the derivatives of 4-carboxy-2-pyrrolidinone corresponding to formula (I) below or a salt thereof, optical isomers, stereoisomers, enantiomers and diastereoisomers thereof or a geometric isomer thereof:

[formula 44]

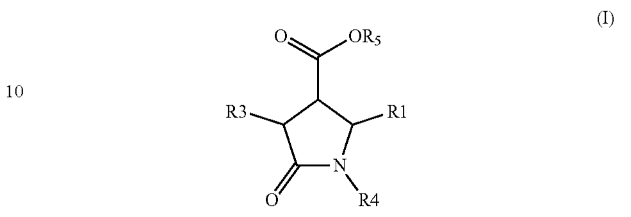

in which:

R1 and R3 represent, independently of each other, a hydrogen atom or a linear or branched $C_1$-$C_6$, preferably $C_1$-$C_4$ alkyl radical, R4 represents a hydrogen atom or a linear or branched $C_1$-$C_6$ alkyl radical, R5 represents a hydrogen atom or a linear or branched $C_1$-$C_6$ alkyl radical, when $R_3$ is hydrogen, the compounds could be in the free acid form thereof or in the form of the cosmetically acceptable salts thereof, may be obtained:

either by the condensation of a diester of itaconic acid of formula (II) with a primary amine of formula (III), with or without solvent, at a temperature of between 20° C. and 150° C., according to the following scheme:

[formula 45]

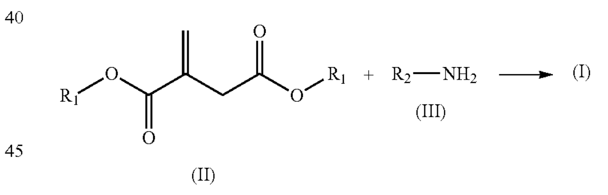

or in 2 steps starting from itaconic acid of formula (IV) by condensation with the primary amine of formula (III) optionally in the presence of a solvent, in order to give the intermediate acid of formula (V), followed by an esterification of this acid of formula (V) in the presence of an excess of alcohol of formula (VI), according to the following scheme:

[formula 46]

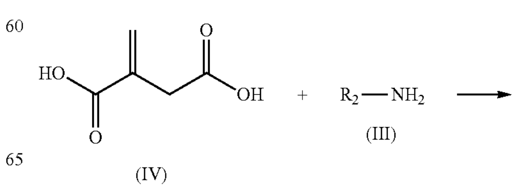

-continued

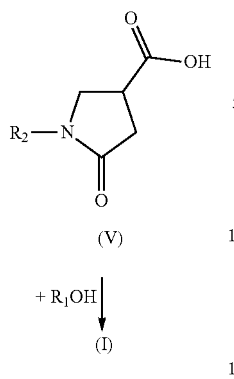

(V)

(I)

According to a particular embodiment of the invention, the compound(s) chosen from gamma-butyrolactones and gamma-butyrolactams as defined previously is (are) present in the composition in a content ranging from 0.1% to 99%, preferably from 0.1% to 50% by weight, preferably from 1% to 30%, even more preferentially from 1% to 10%, better still from 1% to 5% by weight relative to the total weight of the composition.

According to a particular embodiment of the invention, the weight ratio of the total amount of compounds chosen from gamma-butyrolactones and gamma-butyrolactams of formula (38) to the total amount of merocyanines of formula (3) is greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a first preferred embodiment, the composition in accordance with the invention comprises the compound (25) as the merocyanine of formula (3) and the compound of formula (39) as the compound chosen from gamma-butyrolactones and gamma-butyrolactams, with a weight ratio of the amount of compound (39) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a second preferred embodiment, the composition in accordance with the invention comprises the compound (25) as the merocyanine of formula (3) and the compound of formula (40) as the compound chosen from gamma-butyrolactones and gamma-butyrolactams, with a weight ratio of the amount of compound (40) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a third preferred embodiment of the invention, the composition in accordance with the invention comprises the compound (25) as the merocyanine of formula (3) and the compound of formula (41) as the compound chosen from gamma-butyrolactones and gamma-butyrolactams, with a weight ratio of the amount of compound (41) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a fourth preferred embodiment, the composition in accordance with the invention comprises compound (25) as the merocyanine of formula (3) and the compound of formula (42) as the compound chosen from gamma-butyrolactones and gamma-butyrolactams, with a weight ratio of the amount of compound (42) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a fifth preferred embodiment, the composition in accordance with the invention comprises the compound (25) as the merocyanine of formula (3) and the compound of formula (43) as the compound chosen from gamma-butyrolactones and gamma-butyrolactams, with a weight ratio of the amount of compound (43) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to a sixth preferred embodiment of the invention, the composition in accordance with the invention comprises the compound (25) as the merocyanine of formula (3) and the compound of formula (43a) as the compound chosen from gamma-butyrolactones and gamma-butyrolactams, with a weight ratio of the amount of compound (43a) to the amount of compound (25) of greater than or equal to 0.2/1, preferably greater than 0.5/1, even more preferentially greater than 1/1, better still greater than or equal to 2/1, even better still greater than or equal to 4/1, or indeed greater than or equal to 8/1, more preferably greater than or equal to 9/1, and even better still greater than or equal to 10/1.

According to another particular embodiment of the invention, the weight ratio of the total amount of compounds chosen from gamma-butyrolactones and gamma-butyrolactams of formula (38) to the total amount of merocyanines of formula (3) is less than or equal to 50/1, preferably less than or equal to 40/1, even more preferentially less than or equal to 30/1, better still less than or equal to 20/1.

According to a first preferred embodiment, the composition in accordance with the invention comprises the compound (25) as the merocyanine of formula (3) and the compound of formula (39) as the compound chosen from gamma-butyrolactones and gamma-butyrolactams, with a weight ratio of the amount of compound (39) to the amount of compound (25) of less than or equal to 50/1, preferably less than or equal to 40/1, even more preferentially less than or equal to 30/1, better still less than or equal to 20/1.

According to a second preferred embodiment, the composition in accordance with the invention comprises the compound (25) as the merocyanine of formula (3) and the compound of formula (40) as the compound chosen from gamma-butyrolactones and gamma-butyrolactams, with a weight ratio of the amount of compound (40) to the amount of compound (25) of less than or equal to 50/1, preferably less than or equal to 40/1, even more preferentially less than or equal to 30/1, better still less than or equal to 20/1.

According to a third preferred embodiment of the invention, the composition in accordance with the invention comprises the compound (25) as the merocyanine of formula (3) and the compound of formula (41) as the compound chosen from gamma-butyrolactones and gamma-butyrolactams, with a weight ratio of the amount of compound (41) to the amount of compound (25) of less than or equal to 50/1, preferably less than or equal to 40/1, even more preferentially less than or equal to 30/1, better still less than or equal to 20/1.

According to a fourth preferred embodiment, the composition in accordance with the invention comprises the compound (25) as the merocyanine of formula (3) and the compound of formula (42) as the compound chosen from gamma-butyrolactones and gamma-butyrolactams, with a weight ratio of the amount of compound (42) to the amount of compound (25) of less than or equal to 50/1, preferably less than or equal to 40/1, even more preferentially less than or equal to 30/1, better still less than or equal to 20/1.

According to a fifth preferred embodiment, the composition in accordance with the invention comprises the compound (25) as the merocyanine of formula (3) and the compound of formula (43) as the compound chosen from gamma-butyrolactones and gamma-butyrolactams, with a weight ratio of the amount of compound (43) to the amount of compound (25) of less than or equal to 50/1, preferably less than or equal to 40/1, even more preferentially less than or equal to 30/1, better still less than or equal to 20/1.

According to a sixth preferred embodiment of the invention, the composition in accordance with the invention comprises the compound (25) as the merocyanine of formula (3) and the compound of formula (43a) as the compound chosen from gamma-butyrolactones and gamma-butyrolactams, with a weight ratio of the amount of compound (43a) to the amount of compound (25) of less than or equal to 50/1, preferably less than or equal to 40/1, even more preferentially less than or equal to 30/1, better still less than or equal to 20/1.

Fatty Phase

The composition in accordance with the invention can comprise at least one fatty phase.

For the purposes of the invention, the term "fatty phase" is understood to mean a phase comprising at least one fatty substance, which is notably liquid, solid or pasty, and all of the liposoluble and lipophilic ingredients used for the formulation of the compositions of the invention.

According to one particular embodiment, the composition according to the invention comprises at least one oil.

The term "oil" is understood to mean any fatty substance in the liquid form at ambient temperature (20-25° C.) and at atmospheric pressure (760 mmHg).

The fatty phase can comprise notably at least one volatile or nonvolatile hydrocarbon oil and/or one volatile or nonvolatile silicone oil and/or one volatile or nonvolatile fluoro oil.

For the purposes of the present invention, the term "silicone oil" means an oil comprising at least one silicon atom, and notably at least one Si—O group.

The term "hydrocarbon oil" is understood to mean an oil mainly containing hydrogen and carbon atoms and optionally one or more heteroatoms, in particular nitrogen and oxygen. Thus, these oils may in particular contain one or more carboxyl, ester, ether, hydroxyl functions.

The term "fluoro oil" refers to an oil comprising at least one fluorine atom.

For the purposes of the invention, the term "volatile oil" is intended to mean an oil that is capable of evaporating on contact with the skin or the keratin fibre in less than one hour, at ambient temperature and atmospheric pressure. The volatile oil(s) of the invention are volatile cosmetic oils, which are liquid at ambient temperature, having a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is understood to mean an oil which remains on the skin or the keratin fibre at ambient temperature and atmospheric pressure for at least several hours and which has in particular a vapour pressure of less than $10^{-3}$ mmHg (0.13 Pa).

Hydrocarbon Oils

The composition in accordance with the invention comprises at least one ester of $C_2$-$C_{22}$ di- or tricarboxylic acid and of $C_1$-$C_{24}$ alcohols.

The $C_2$-$C_{22}$ di- or tricarboxylic acids are in particular chosen from citric acid, malic acid, malonic acid, succinic acid, adipic acid, maleic acid, fumaric acid, tartaric acid, isocitric acid, and mixtures thereof. The acids are preferably citric acid and adipic acid, and even more preferentially the acid is citric acid.

The $C_1$-$C_{24}$ alcohols are not oxyalkylenated. They may be aliphatic, cyclic or aromatic, having from 1 to 24 carbon atoms. They are in particular chosen from phenol, benzyl alcohol, lauryl alcohol, myristyl alcohol, cetyl alcohol, stearyl alcohol, methanol, ethanol, propanol, n-butanol, t-butanol, pentanol and hexanol. Preferably, the alcohol(s) is/are $C_1$-$C_6$ alcohol(s) and can be chosen from methanol, ethanol, propanol, n-butanol, t-butanol, pentanol, hexanol, and even more preferentially the alcohol is ethanol.

The ester(s) of $C_2$-$C_{22}$ di- or tricarboxylic acid and of $C_1$-$C_{24}$ alcohols can be mono- or polyesterified.

Monoesterified is understood to mean that only one of the two or three carboxylic acid functions is esterified. Polyesterified is understood to mean that at least two carboxylic acid functions are esterified.

The di- or tricarboxylic acid can be esterified with several different alcohols. It is preferably esterified with just one alcohol.

According to a particular embodiment of the invention, the composition comprises at least one ester of $C_3$-$C_{22}$ tricarboxylic acid and of $C_1$-$C_{24}$, preferably $C_1$-$C_6$, alcohols. This/these ester(s) can be mono-, di- or triesterified.

Monoesterified is understood to mean that only one of the three carboxylic acid functions is esterified. Diesterified is understood to mean that two of the three carboxylic acid functions are esterified. Triesterified is understood to mean that all three carboxylic acid functions are esterified.

According to a particular embodiment of the invention, the ester(s) of $C_3$-$C_{22}$ tricarboxylic acid and of $C_1$-$C_6$ alcohols are triesterified.

According to a particular embodiment of the invention, the ester(s) of $C_3$-$C_{22}$ tricarboxylic acid and of $C_1$-$C_6$ alcohols are chosen from the compounds of formula (47) below:

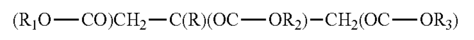

$$(R_1O—CO)CH_2—C(R)(OC—OR_2)—CH_2(OC—OR_3)$$

in which:

$R_1$, $R_2$ and $R_3$ represent, independently of each other, a hydrogen atom or a monovalent, saturated or unsaturated, aliphatic, cyclic or aromatic hydrocarbon group having from 1 to 6 carbon atoms;

R represents a hydrogen atom or a hydroxyl radical.

According to a preferred embodiment, $R_1$, $R_2$ and $R_3$ represent, independently of each other, a hydrogen atom or a linear or branched, substituted or unsubstituted, preferably unsubstituted, $C_1$-$C_6$ alkyl radical, and in particular a radical chosen from methyl, ethyl, propyl, n-butyl, t-butyl, pentyl and hexyl radicals. Preferably, $R_1$, $R_2$ and $R_3$ are chosen, independently of each other, from a hydrogen atom and methyl, ethyl, propyl, n-butyl and t-butyl radicals.

According to a preferred embodiment of the invention, the radicals $R_1$, $R_2$ and $R_3$ are identical and are chosen from $C_1$-$C_6$, preferably $C_1$-$C_4$, alkyl radicals and even more preferentially are ethyl radicals.

According to a preferred embodiment of the invention, R represents a hydroxyl radical.

According to a particular embodiment of the invention, the ester of tricarboxylic acid and of $C_1$-$C_6$ alcohols has the following formula:

[Formula 48]

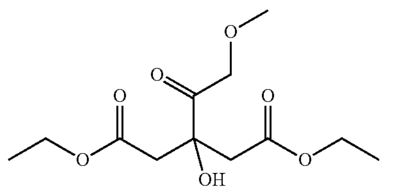

As an example of an ester of $C_3$-$C_{22}$ tricarboxylic acid and of $C_1$-$C_6$ alcohols of formula (48) and having the INCI name Triethyl Citrate, mention will be made of the product sold under the name Citrofol Al Extra by Jungbunzlauer.

Mention may notably be made, as non-volatile hydrocarbon oils which can be used according to the invention, of:

(i) hydrocarbon oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, red kuri squash oil, pumpkin oil, blackcurrant oil, evening primrose oil, millet oil, barley oil, quinoa oil, rye oil, safflower oil, candlenut oil, passionflower oil or musk rose oil; or alternatively triglycerides of caprylic/capric acids, such as those sold by Stearinerie Dubois or those sold under the names Miglyol 810®, 812® and 818® by Dynamit Nobel;

(ii) synthetic ethers having from 10 to 40 carbon atoms;

(iii) linear or branched hydrocarbons of mineral or synthetic origin, such as liquid petroleum, polydecenes, hydrogenated polyisobutene, such as Parleam, squalane and mixtures thereof;

(iv) synthetic esters, such as the oils of formula RCOOR' wherein R represents the residue of a linear or branched fatty acid comprising from 1 to 40 carbon atoms and R' represents a hydrocarbon chain, in particular branched hydrocarbon chain, containing from 1 to 40 carbon atoms, with the proviso that $R+R'\geq 10$, such as, for example, Purcellin oil (cetostearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226® by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name Dub Dis by Stéarinerie Dubois, octanoates, decanoates or ricinoleates of alcohols or of polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; acetates;

(v) fatty alcohols which are liquid at ambient temperature, comprising a branched and/or unsaturated carbon-based chain having from 12 to 26 carbon atoms, such as octyldodecanol, isostearyl alcohol, oleyl alcohol, 2-hexyldecanol, 2-butyloctanol or 2-undecylpentadecanol;

(vi) higher $C_{12}$-$C_{22}$ fatty acids, such as oleic acid, linoleic acid or linolenic acid;

(vii) carbonates, such as dicaprylyl carbonate, such as the product sold under the name Cetiol CC® by Cognis;

and mixtures thereof.

Among the nonvolatile hydrocarbon oils which can be used according to the invention, preference will be given more particularly to glyceride triesters and in particular to caprylic/capric acid triglycerides, synthetic esters and in particular diisopropyl adipate, diisopropyl sebacate, isopropyl palmitate, dicaprylyl carbonate, isononyl isononanoate, oleyl erucate, $C_{12}$-$C_{15}$ alkyl benzoate, 2-ethylphenyl benzoate and fatty alcohols, in particular octyldodecanol. Preferably, the nonvolatile hydrocarbon oils are chosen from diisopropyl adipate, diisopropyl sebacate, isopropyl palmitate and dicaprylyl carbonate.

As volatile hydrocarbon oils which can be used according to the invention, mention may be made in particular of hydrocarbon oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/155 059 (mixtures of different alkanes differing by at least one carbon). These alkanes are obtained from fatty alcohols, themselves obtained from coconut or palm oil. Mention may be made of the mixtures of n-undecane ($C_{11}$) and n-tridecane ($C_{13}$) obtained in Examples 1 and 2 of application WO2008/155059 of Cognis. Mention may also be made of n-dodecane ($C_{12}$) and n-tetradecane ($C_{14}$) sold by Sasol respectively under the references Parafol 12-97 and Parafol 14-97®, and also mixtures thereof.

Other volatile hydrocarbon oils, such as petroleum distillates, in particular those sold under the name Shell Solt® by Shell, can also be used. According to one embodiment, the volatile solvent is chosen from volatile hydrocarbon oils having from 8 to 16 carbon atoms, and mixtures thereof.

Silicone Oils

The nonvolatile silicone oils may be notably chosen from nonvolatile polydimethylsiloxanes (PDMSs), polydimethylsiloxanes including alkyl or alkoxy groups which are pendent and/or at the end of the silicone chain, these groups each containing from 2 to 24 carbon atoms, or phenyl silicones, such as phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxysilicates.

Mention may be made, as volatile silicone oils, for example, of volatile linear or cyclic silicone oils, in particular those having a viscosity ≤8 centistokes ($8\times10^{-6}$ $m^2/s$) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

A fatty phase according to the invention can additionally comprise other fatty substances, mixed with or dissolved in the oil.

Another fatty substance which can be present in the fatty phase can, for example, be:

- a fatty acid chosen from fatty acids comprising from 8 to 30 carbon atoms, such as stearic acid, lauric acid, palmitic acid and oleic acid;
- a wax chosen from waxes such as lanolin, beeswax, carnauba or candelilla wax, rice bran wax, paraffin waxes, lignite waxes, microcrystalline waxes, ceresin or ozokerite, or synthetic waxes, such as polyethylene waxes or Fischer-Tropsch waxes;
- a gum chosen from silicone gums (dimethiconol);
- a pasty compound, such as polymeric or non-polymeric silicone compounds, esters of a glycerol oligomer, arachidyl propionate, fatty acid triglycerides and derivatives thereof;
- and mixtures thereof.

Preferentially, the overall fatty phase, including all the lipophilic substances other than lipophilic screening agents of the composition capable of being dissolved in this same phase, represents from 5% to 95% by weight and preferentially from 10% to 80% by weight, relative to the total weight of the composition.

Aqueous Phase

The composition in accordance with the invention can comprise at least one aqueous phase.

The aqueous phase contains water and optionally other water-soluble or water-miscible organic solvents.

An aqueous phase which is suitable for the invention can comprise, for example, a water chosen from a natural spring water, such as water from La Roche-Posay, water from Vittel, water from Saint-Gervais Mont-Blanc or waters from Vichy, or a floral water.

According to one specific form of the invention, the overall aqueous phase, including all the hydrophilic substances other than hydrophilic screening agents of the composition capable of being dissolved in this same phase, represents from 1% to 99% by weight and preferentially from 10% to 80% by weight, relative to the total weight of the composition.

Additives

Additional UV-Screening Agents

The compositions according to the invention may also contain one or more additional UV-screening agents chosen from hydrophilic, lipophilic or insoluble organic UV-screening agents and/or one or more mineral pigments. It will preferentially be constituted of at least one hydrophilic, lipophilic or insoluble organic UV-screening agent.

The term "hydrophilic UV-screening agent" is intended to mean any cosmetic or dermatological organic or inorganic compound for screening out UV radiation, which can be fully dissolved in molecular form in a liquid aqueous phase or else which can be solubilized in colloidal form (for example in micellar form) in a liquid aqueous phase.

The term "lipophilic screening agent" is intended to mean any cosmetic or dermatological organic or inorganic compound for screening out UV radiation, which can be fully dissolved in molecular form in a liquid fatty phase or else which can be solubilized in colloidal form (for example in micellar form) in a liquid fatty phase.

The term "insoluble UV-screening agent" is intended to mean any cosmetic or dermatological organic or inorganic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by Dynamit Nobel. This solubility, determined at 70° C., is defined as the amount of product in solution in the solvent at equilibrium with an excess of solid in suspension after returning to ambient temperature. It can be easily evaluated in the laboratory.

The additional organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in patent U.S. Pat. No. 5,624,663; benzimidazole derivatives; imidazoline compounds; bis-benzazolyl compounds, such as described in patents EP 669 323 and U.S. Pat. No. 2,463,264; p-aminobenzoic (PABA) compounds; methylenebis(hydroxyphenylbenzotriazole) compounds, such as described in applications U.S. Pat. Nos. 5,237,071, 5,166,355, GB 2 303 549, DE 197 26 184 and EP 893 119; benzoxazole compounds, such as described in patent applications EP 0 832 642, EP 1 027 883, EP 1 300 137 and DE 101 62 844; screening polymers and screening silicones, such as those described in particular in application WO 93/04665; dimers derived from α-alkylstyrene, such as those described in patent application DE 198 55 649; 4,4-diarylbutadiene compounds, such as described in applications EP 0 967 200, DE 197 46 654, DE 197 55 649, EP-A-1 008 586, EP 1 133 980 and EP 133 981, and mixtures thereof.

Mention may be made, as examples of organic photoprotective agents, of those denoted below under their INCI names.

Cinnamic Compounds

- Ethylhexyl Methoxycinnamate, sold in particular under the trade name Parsol MCX® by DSM Nutritional Products,
- Isopropyl Methoxycinnamate,
- Isoamyl p-Methoxycinnamate, sold under the trade name Neo Heliopan E 1000® by Symrise,
- DEA Methoxycinnamate,
- Diisopropyl Methylcinnamate,
- Glyceryl Ethylhexanoate Dimethoxycinnamate.

Dibenzoylmethane Compounds

- Butyl Methoxydibenzoylmethane, sold in particular under the trade name Parsol 1789® by DSM Nutritional Products,
- Isopropyl Dibenzoylmethane.

Para-Aminobenzoic Compounds

PABA,

Ethyl PABA,

Ethyl Dihydroxypropyl PABA,

Ethylhexyl Dimethyl PABA, sold in particular under the name Escalol 507® by ISP, Glyceryl PABA, PEG-25 PABA, sold under the name Uvinul P 25® by BASF.

Salicylic Compounds

Homosalate, sold under the name Eusolex HMS® by Rona/EM Industries,

Ethylhexyl Salicylate, sold under the name Neo Heliopan OS® by Symrise,

Dipropylene Glycol Salicylate, sold under the name Dipsal® by Scher,

TEA Salicylate, sold under the name Neo Heliopan TS® by Symrise.

β,β-Diphenylacrylate Compounds

Octocrylene, sold in particular under the trade name Uvinul N 539® by BASF,

Etocrylene, sold in particular under the trade name Uvinul N 35® by BASF.

Benzophenone Compounds

Benzophenone-1, sold under the trade name Uvinul 400® by BASF,

Benzophenone-2, sold under the trade name Uvinul D 50® by BASF,

Benzophenone-3 or Oxybenzone, sold under the trade name Uvinul M 40® by BASF,

Benzophenone-4, sold under the trade name Uvinul MS 40® by BASF,

Benzophenone-5,

Benzophenone-6, sold under the trade name Helisorb 11® by Norquay,

Benzophenone-8, sold under the trade name Spectra-Sorb UV-24® by American Cyanamid, Benzophenone-9, sold under the trade name Uvinul DS 49® by BASF, Benzophenone-12, n-Hexyl 2-(4-diethylamino-2-hydroxybenzoyl)benzoate, sold under the trade name Uvinul A Plus® or, as a mixture with octyl methoxycinnamate, under the trade name Uvinul A Plus BR by BASF, 1,1'-(1,4-Piperazinediyl)bis[1-[2-[4-(diethylamino)-2-hydroxybenzoyl]phenyl]methanone] (CAS 919803-06-8), as described in application WO 2007/071584; this compound advantageously being used in micronized form (mean size of 0.02 to 2 μm), which may be obtained, for example, according to the micronization process described in applications GB-A-2 303 549 and EP-A-893 119, and in particular in the form of an aqueous dispersion.

Benzylidenecamphor Compounds

3-Benzylidene Camphor, manufactured under the name Mexoryl SD® by Chimex,

4-Methylbenzylidene Camphor, sold under the name Eusolex 6300® by Merck,

Benzylidene Camphor Sulfonic Acid, manufactured under the name Mexoryl SL® by Chimex, Camphor Benzalkonium Methosulfate, manufactured under the name Mexoryl SO® by Chimex, Terephthalylidene Dicamphor Sulfonic Acid, manufactured under the name Mexoryl SX® by Chimex, Polyacrylamidomethyl Benzylidene Camphor, manufactured under the name Mexoryl SW® by Chimex.

Phenylbenzimidazole Compounds

Phenylbenzimidazole Sulfonic Acid, sold in particular under the trade name Eusolex 232® by Merck.

Bis-Benzazolyl Compounds

Disodium Phenyl Dibenzimidazole Tetrasulfonate, sold under the trade name Neo Heliopan AP® by Haarmann and Reimer.

Phenylbenzotriazole Compounds

Drometrizole Trisiloxane, sold under the name Silatrizole® by Rhodia Chimie.

Methylenebis(hydroxyphenylbenzotriazole) Compounds

Methylene Bis-Benzotriazolyl Tetramethylbutylphenol, in particular in solid form, such as the product sold under the trade name Mixxim BB/100® by Fairmount Chemical, or in the form of an aqueous dispersion of micronized particles having a mean particle size which varies from 0.01 to 5 μm, more preferentially from 0.01 to 2 μm and more particularly from 0.020 to 2 μm, with at least one alkyl polyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and varies from 1.4 to 1.6, such as described in patent GB-A-2 303 549, sold in particular under the trade name Tinosorb M® by BASF, or in the form of an aqueous dispersion of micronized particles having a mean particle size which varies from 0.02 to 2 μm, more preferentially from 0.01 to 1.5 μm and more particularly from 0.02 to 1 μm, in the presence of at least one polyglyceryl mono($C_8$-$C_{20}$) alkyl ester having a degree of glycerol polymerization of at least 5, such as the aqueous dispersions described in application WO 2009/063392.

Triazine Compounds 3,3'-(1,4-Phenylene)bis(5,6-diphenyl-1,2,4-triazine), with the INCI name Phenylene Bis-Diphenyltriazine, and with the following chemical structure:

[formula 49]

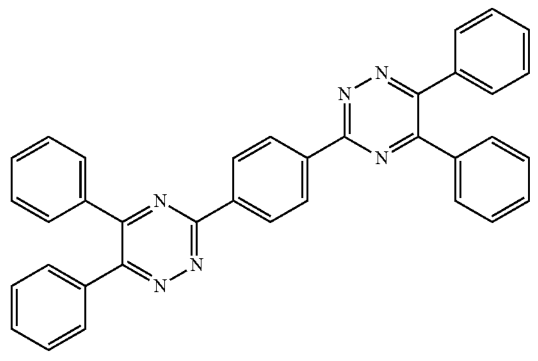

Bis-Ethylhexyloxyphenol Methoxyphenyl Triazine, sold under the trade name Tinosorb S® by BASF, Ethylhexyl Triazone, sold in particular under the trade name Uvinul T 150® by BASF, Diethylhexyl Butamido Triazone, sold under the trade name Uvasorb HEB® by Sigma 3V, 2,4,6-tris(dineopentyl 4'-aminobenzalmalonate)-s-triazine, 2,4,6-tris(diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, symmetrical triazine screening agents substituted by naphthalenyl groups or polyphenyl groups described in patent U.S. Pat. No. 6,225,467, application WO2004/085412 (see compounds 6 and 9) or the document "Symmetrical Triazine Derivatives", IP.COM IPCOM000031257 Journal, INC West Henrietta, NY, US (20 Sep. 2004), in particular 2,4,6-tris(diphenyl) triazine and 2,4,6-tris(terphenyl)triazine, which is also mentioned in patent applications WO06/035000, WO06/034982, WO06/034991, WO06/035007, WO2006/034992 and WO2006/034985, these compounds advantageously being used in micronized form (mean particle size of 0.02 to 3 μm), which can be obtained, for example, according to the micronization process described in applications GB-A-2 303 549 and EP-A-893 119, and in particular in aqueous dispersion form, silicone triazines substituted by two aminobenzoate groups, such as described in patent EP 0 841 341, in particular 2,4-bis(n-butyl 4'-aminobenzalmalonate)-6-[(3-{1,3,3,3-tetramethyl-1-[(trimethylsilyl)oxy] disiloxanyl}propyl)amino]-s-triazine.

Anthranilic Compounds

Menthyl anthranilate, sold under the trade name Neo Heliopan MA® by Symrise.

Imidazoline Compounds

Ethylhexyl Dimethoxybenzylidene Dioxoimidazoline Propionate.

Benzalmalonate Compounds

Polyorganosiloxane comprising benzalmalonate functional groups, such as Polysilicone-15, sold under the trade name Parsol SLX® by Hoffmann-La Roche.

4,4-Diarylbutadiene Compounds 1,1-Dicarboxy(2,2'-dimethylpropyl)-4,4-diphenylbutadiene.

Benzoxazole Compounds 2,4-Bis[5-(1-dimethylpropyl)benzoxazol-2-yl(4-phenyl) imino]-6-(2-ethylhexyl)imino-1,3,5-triazine, sold under the name Uvasorb K2A® by Sigma 3V.

The preferential organic screening agents are chosen from:

Ethylhexyl Methoxycinnamate,
Ethylhexyl Salicylate,
Homosalate,
Butyl Methoxydibenzoylmethane,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene Camphor,
Terephthalylidene Dicamphor Sulfonic Acid,
Disodium Phenyl Dibenzimidazole Tetrasulfonate,
Methylene Bis-Benzotriazolyl Tetramethylbutylphenol,
Bis-Ethylhexyloxyphenol Methoxyphenyl Triazine,
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl) amino]-s-triazine,
2,4,6-Tris(diphenyl)triazine,
2,4,6-Tris(terphenyl)triazine,
Drometrizole Trisiloxane,
Polysilicone-15,
1,1-Dicarboxy(2,2'-dimethylpropyl)-4,4-diphenylbutadiene,
2,4-Bis[5-(1-dimethylpropyl)benzoxazol-2-yl(4-phenyl) imino]-6-(2-ethylhexyl)imino-1,3,5-triazine
and mixtures thereof.

The particularly preferred organic screening agents are chosen from:

Ethylhexyl Salicylate,
Homosalate,
Butyl Methoxydibenzoylmethane,
Octocrylene,
n-Hexyl 2-(4-diethylamino-2-hydroxybenzoyl)benzoate,
Terephthalylidene Dicamphor Sulfonic Acid,
Bis-Ethylhexyloxyphenol Methoxyphenyl Triazine,
Ethylhexyl Triazone,
Diethylhexyl Butamido Triazone,
2,4-Bis(n-butyl 4'-aminobenzalmalonate)-6-[(3-{1,3,3,3-tetramethyl-1-[(trimethylsilyl)oxy]disiloxanyl}propyl) amino]-s-triazine,
Drometrizole Trisiloxane,
and mixtures thereof.

The inorganic UV-screening agents used in accordance with the present invention are metal oxide pigments. More preferentially, the inorganic UV-screening agents of the invention are metal oxide particles having a mean elementary particle size of less than or equal to 0.5 μm, more preferentially of between 0.005 and 0.5 μm, more preferentially still of between 0.01 and 0.2 μm, better still between 0.01 and 0.1 μm and more particularly between 0.015 and 0.05 μm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments which have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

The coated pigments are more particularly titanium oxides coated:

with silica, such as the product Sunveil® from Ikeda, with silica and iron oxide, such as the product Sunveil F® from Ikeda, with silica and alumina, such as the products Microtitanium Dioxide MT 500 SA® and Microtitanium Dioxide MT 100 SA from Tayca and Tioveil from Tioxide, with alumina, such as the products Tipaque TTO-55 (B)® and Tipaque TTO-55 (A)® from Ishihara and UVT 14/4 from Sachtleben Pigments, with alumina and aluminium stearate, such as the products Microtitanium Dioxide MT 100 T®, MT 100 TX®, MT 100 Z® and MT-01® from Tayca, the products Solaveil CT-10 W® and Solaveil CT 100® from Uniqema and the product Eusolex T-AVO® from Merck, with silica, alumina and alginic acid, such as the product MT-100 AQ® from Tayca, with alumina and aluminium laurate, such as the product Microtitanium Dioxide MT 100 S® from Tayca, with iron oxide and iron stearate, such as the product Microtitanium Dioxide MT 100 F® from Tayca, with zinc oxide and zinc stearate, such as the product BR 351® from Tayca, with silica and alumina and treated with a silicone, such as the products Microtitanium Dioxide MT 600 SAS®, Microtitanium Dioxide MT 500 SAS® or Microtitanium Dioxide MT 100 SAS® from Tayca, with silica, alumina and aluminum stearate and treated with a silicone, such as the product STT-30-DS® from Titan Kogyo, with silica and treated with a silicone, such as the product UV-Titan X 195® from Sachtleben Pigments, with alumina and treated with a silicone, such as the products Tipaque TTO-55 (S)® from Ishihara or UV Titan M 262® from Sachtleben Pigments, with triethanolamine, such as the product STT-65-S from Titan Kogyo, with stearic acid, such as the product Tipaque TTO-55 (C)® from Ishihara, with sodium hexametaphosphate, such as the product Microtitanium Dioxide MT 150 W® from Tayca, $TiO_2$ treated with octyltrimethylsilane, sold under the trade name T 805® by Degussa Silices, $TiO_2$ treated with a polydimethylsiloxane, sold under the trade name 70250 Cardre UF TiO2SI3® by Cardre, anatase/rutile $TiO_2$ treated with a polydimethylhydrosiloxane, sold under the trade name Micro Titanium Dioxide USP Grade Hydrophobic® by Color Techniques, $TiO_2$ coated with triethylhexanoin, with aluminum stearate and with alumina sold under the trade name Solaveil CT-200-LQ-(WD) by Croda, $TiO_2$ coated with aluminium stearate, with alumina and with silicone sold under the trade name Solaveil CT-12W-LQ-(WD) by Croda, $TiO_2$ coated with lauroyl lysine sold by Daito Kasei Kogyo under the name LL 5 Titanium Dioxyde CR 50, $TiO_2$ coated with C9-15 fluoroalcohol phosphate and with aluminium hydroxide sold by Daito Kasei Kogyo under the name PFX-5 TiO2 CR-50.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides, including those of capric/caprylic acids. The oily dispersion of titanium oxide particles can additionally comprise one or more dispersing agents, such as, for example, a sorbitan ester, such as sorbitan isostearate, a polyoxyalkylenated glycerol fatty acid ester, such as Tri-PPG-3 Myristyl Ether Citrate and Polyglyceryl-3 Polyricinoleate. Preferably, the oily dispersion of titanium oxide particles comprises at least one dispersing agent chosen from polyoxyalkylenated glycerol fatty acid esters. Mention may more particularly be made of the oily dispersion of $TiO_2$ particles doped with manganese in capric/caprylic acid triglyceride in the presence of Tri-PPG-3 Myristyl Ether Citrate and Polyglyceryl-3 Polyricinoleate and Sorbitan Isostearate with the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by Tayca under the trade names Microtitanium Dioxide MT 500 B or Microtitanium Dioxide MT 600 B®, by Degussa under the name P 25, by Wackher under the name Transparent titanium oxide PW®, by Miyoshi Kasei under the name UFTR®, by Tomen under the name ITS® and by Tioxide under the name Tioveil AQ.

The uncoated zinc oxide pigments are, for example:

those sold under the name Z-Cote by Sunsmart;

those sold under the name Nanox® by Elementis;

those sold under the name Nanogard WCD 2025® by Nanophase Technologies.

The coated zinc oxide pigments are, for example:

those sold under the name Zinc Oxide CS-5® by Toshibi (ZnO coated with polymethylhydrosiloxane);

those sold under the name Nanogard Zinc Oxide FN® by Nanophase Technologies (as a 40% dispersion in Finsolv TN®, $C_{12}$-$C_{15}$ alkyl benzoates);

those sold under the name Daitopersion Zn-30® and Daitopersion Zn-50® by Daito (dispersions in oxyethylenated cyclopolymethylsiloxane/polydimethylsiloxane, containing 30% or 50% of zinc oxides coated with silica and polymethylhydrosiloxane);

those sold under the name NFD Ultrafine ZnO® by Daikin (ZnO coated with perfluoroalkyl phosphate and copolymer based on perfluoroalkylethyl in dispersion in cyclopentasiloxane);

those sold under the name SPD-Z1® by Shin-Etsu (ZnO coated with silicone-grafted acrylic polymer, dispersed in cyclodimethylsiloxane);

those sold under the name Escalol Z100® by ISP (alumina-treated ZnO dispersed in the ethylhexyl methoxycinnamate/PVP-hexadecene copolymer/methicone mixture);

those sold under the name Fuji ZnO-SMS-10® by Fuji Pigment (ZnO coated with silica and polymethylsilsesquioxane);

those sold under the name Nanox Gel TN® by Elementis (ZnO dispersed at 55% in $C_{12}$-$C_{15}$ alkyl benzoates with hydroxystearic acid polycondensate).

The uncoated cerium oxide pigments may be, for example, those sold under the name Colloidal Cerium Oxide® by Rhône-Poulenc.

The uncoated iron oxide pigments are, for example, sold by Arnaud under the names Nanogard WCD 2002® (FE 45B®), Nanogard Iron FE 45 BL AQ, Nanogard FE 45R AQ® and Nanogard WCD 2006® (FE 45R®) or by Mitsubishi under the name TY-220®.

The coated iron oxide pigments are, for example, sold by Arnaud under the names Nanogard WCD 2008 (FE 45B FN)®, Nanogard WCD 2009® (FE 45B 556®), Nanogard FE 45 BL 345® and Nanogard FE 45 BL® or by BASF under the name Transparent Iron Oxide®.

Mention may also be made of mixtures of metal oxides, in particular of titanium dioxide and cerium dioxide, including the mixture in equal weights of titanium dioxide and cerium dioxide coated with silica, sold by Ikeda under the name Sunveil A®, and also the mixture of titanium dioxide and zinc dioxide coated with alumina, silica and silicone, such as the product M 261® sold by Sachtleben Pigments, or coated with alumina, silica and glycerol, such as the product M 211® sold by Sachtleben Pigments.

According to the invention, coated or uncoated titanium oxide pigments are particularly preferred.

The additional UV-screening agents according to the invention can be present in the composition according to the invention in a content ranging from 0.1% to 60% by weight and in particular from 5% to 30% by weight relative to the total weight of the composition.

Other Additives

The composition in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Among the organic solvents, mention may be made of short-chain monoalcohols, for example $C_1$-$C_4$ monoalcohols, such as ethanol and isopropanol, short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, hexylene glycol, dipropylene glycol or diethylene glycol, 2-ethoxyethanol, diethylene glycol monomethyl ether, triethylene glycol monomethyl ether, sorbitol, and mixtures thereof.

According to a preferred embodiment, use may more particularly be made of ethanol, propylene glycol, glycerol, and mixtures thereof.

Mention may be made, as thickeners, of carboxyvinyl polymers, such as the Carbopols® (Carbomers) and the Pemulens, such as Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13-14}$ isoparaffin/Laureth 7) or Simulgel 600 (CTFA name: acrylamide/sodium acryloyldimethyl taurate copolymer/isohexadecane/polysorbate 80) by SEPPIC; 2-acrylamido-2-methylpropanesulfonic acid polymers and copolymers, optionally crosslinked and/or neutralized, such as the poly (2-acrylamido-2-methylpropanesulfonic acid) sold by Hoechst under the trade name Hostacerin AMPS® (CTFA name: ammonium polyacryloyldimethyl taurate) or Simulgel 800®, sold by SEPPIC (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS® and Sepinov EMT 10®, sold by SEPPIC; cellulose derivatives, such as hydroxyethylcellulose; polysaccharides and in particular gums, such as xanthan gum; water-soluble or water-dispersible silicone derivatives, such as acrylic silicones, polyether silicones and cationic silicones, and mixtures thereof.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents chosen from alkanolamines, in particular triethanolamine, and sodium hydroxide.

Among the active agents for caring for keratin materials such as the skin, the lips, the scalp, the hair, the eyelashes or the nails, mention may be made for example of vitamins and derivatives or precursors thereof, alone or as mixtures; antioxidants; free-radical scavengers; anti-pollutants; self-tanning agents; anti-glycation agents; calmatives; deodorant agents; essential oils; NO-synthase inhibitors; agents for stimulating the synthesis of dermal or epidermal macromolecules and/or for preventing degradation thereof; agents for stimulating fibroblast proliferation; agents for stimulating keratinocyte proliferation; muscle relaxants; refreshing agents; tensioning agents; mattifying agents; depigmenting agents; propigmenting agents; keratolytic agents; desquamating agents; moisturizing agents; anti-inflammator antimicrobials; thinning agents; agents which act on cell energy metabolism; insect repellents; substance P antagonists or CRGP antagonists; agents for preventing hair loss; anti-wrinkle agents; anti-ageing agents.

Those skilled in the art will select said active agent(s) as a function of the effect desired on the skin, the hair, the eyelashes, the eyebrows and the nails.

Needless to say, those skilled in the art will take care to select the abovementioned optional additional compound(s) and/or the amounts thereof so that the advantageous properties intrinsically associated with the compositions in accordance with the invention are not, or not substantially, adversely affected by the envisaged addition(s).

Presentation Forms

The compositions in accordance with the invention may be aqueous or anhydrous.

When the compositions are aqueous, they contain at least one aqueous phase.

They can then be in purely aqueous form, that is to say they comprise an amount of fatty phase of less than 10% by weight, preferably less than 5% by weight and even more preferentially less than 2% by weight, relative to the total weight of the composition. Advantageously, the composition in accordance with the invention is essentially aqueous, i.e. it does not contain a fatty phase.

The compositions according to the invention may also be in the form of a simple or complex (O/W, W/O, O/W/O or W/O/W) emulsion, such as a cream, a milk or a gel-cream.

In the case where the composition in accordance with the invention is aqueous, and it is possible to measure its pH, this pH is generally between 3 and 12 approximately, preferably between 5 and 9 approximately, and even more particularly from 5.5 to 8.

The compositions may also be in anhydrous form, such as for example in the form of an oil, a glycolic solution or an alcoholic solution. The term "anhydrous composition" is intended to mean a composition containing less than 1% by weight of water, or even less than 0.5% water, and especially free of water, the water not being added during the preparation of the composition but corresponding to the residual water provided by the mixed ingredients. They can optionally be packaged as an aerosol and be provided in the form of a foam or of a spray.

In the case of compositions in the form of oil-in-water or water-in-oil emulsions, the emulsification processes which can be used are of the paddle or propeller, rotor-stator and HPH type.

In order to obtain stable emulsions with a low content of polymer (oil/polymer ratio >25), it is possible to prepare the dispersion in concentrated phase and then to dilute the dispersion with the remainder of the aqueous phase.

It is also possible, via HPH (between 50 and 800 bar), to obtain stable dispersions with drop sizes that can be as small as 100 nm.

The emulsions generally contain at least one emulsifier chosen from amphoteric, anionic, cationic or nonionic emulsifiers, used alone or as a mixture. The emulsifiers are appropriately chosen according to the emulsion to be obtained (W/O or O/W).

Mention may be made, as examples of W/O emulsifying surfactants, of alkyl esters or ethers of sorbitan, of glycerol, of polyol or of sugars; or silicone surfactants, for instance dimethicone copolyols, such as the mixture of cyclomethicone and dimethicone copolyol sold under the name DC 5225 C® by Dow Corning, and alkyl dimethicone copolyols, such as lauryl methicone copolyol, sold under the name Dow Corning 5200 Formulation Aid by Dow Corning, or cetyl dimethicone copolyol, such as the product sold under the name Abil EM 90R® by Goldschmidt and the mixture of cetyl dimethicone copolyol, polyglyceryl isostearate (4 mol) and hexyl laurate sold under the name Abil WE 09® by Goldschmidt. One or more coemulsifiers, which may be chosen advantageously from the group comprising polyol alkyl esters, may also be added thereto.

Mention may also be made of nonsilicone emulsifying surfactants, notably alkyl esters or ethers of sorbitan, of glycerol, of polyol or of sugars.

Polyol alkyl esters that may in particular be mentioned include polyethylene glycol esters, for instance PEG-30 dipolyhydroxystearate, such as the product sold under the name Arlacel P135® by ICI.

Mention may be made, as glycerol and/or sorbitan esters, for example, of polyglyceryl isostearate, such as the product sold under the name Isolan GI 34® by Goldschmidt; sorbitan isostearate, such as the product sold under the name Arlacel 987® by ICI; sorbitan glyceryl isostearate, such as the product sold under the name Arlacel 986® by ICI, and mixtures thereof.

For the O/W emulsions, examples of non-ionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of a fatty acid and of glycerol, such as the PEG-100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by Henkel under the respective names Plantaren 2000® and Plantaren 1200®, cetostearyl glucoside, optionally as a mixture with cetostearyl alcohol, sold, for example, under the name Montanov 68® by SEPPIC, under the name Tegocare CG90® by Goldschmidt and under the name Emulgade KE3302® by Henkel, and arachidyl glucoside, for example in the form of the mixture of arachidyl and behenyl alcohols and of arachidyl glucoside sold under the name Montanov 202® by SEPPIC. According to a specific embodiment of the invention, the mixture of the alkyl polyglucoside as defined above with the corresponding fatty alcohol can be in the form of a self-emulsifying composition, as described, for example, in document WO-A-92/06778.

When it is an emulsion, the aqueous phase of this emulsion may comprise a nonionic vesicular dispersion prepared according to known processes (Bangham, Standish and Watkins, J. Mol. Biol., 13, 238 (1965), FR 2 315 991 and FR 2 416 008).

The compositions according to the invention find their application in a large number of treatments, in particular cosmetic treatments, for the skin, the lips and the hair, including the scalp, in particular for protecting and/or caring for the skin, the lips and/or the hair, and/or for making up the skin and/or the lips.

Another subject of the present invention is constituted of the use of the compositions according to the invention as defined above in the manufacture of products for the cosmetic treatment of the skin, lips, nails, hair, eyelashes, eyebrows and/or scalp, in particular of care products, sun protection products and makeup products.

The cosmetic compositions according to the invention can be used, for example, as makeup products.

Another subject of the present invention is constituted of a non-therapeutic cosmetic method for caring for and/or making up a keratin material, which consists in applying, to the surface of said keratin material, at least one composition according to the invention as defined above.

Another subject of the invention is constituted of the use of at least one compound chosen from gamma-butyrolactones and gamma-butyrolactams to solubilize a merocyanine of formula (3) as defined above.

According to a particular embodiment, the compounds chosen from gamma-butyrolactones and gamma-butyrolactams make it possible to solubilize the merocyanines in accordance with the invention in the fatty phase and/or in the aqueous phase.

The cosmetic compositions according to the invention can, for example, be used as care products and/or sun protection products for the face and/or body, of liquid to semi-liquid consistency, such as milks, more or less rich creams, cream-gels or pastes. They may optionally be packaged in aerosol form and may be in the form of a foam or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight, relative to the total weight of the composition.

Assembly

According to another aspect, the invention also relates to a cosmetic assembly comprising:

i) a container delimiting one or more compartment(s), said container being closed by a closing member and optionally being unsealed; and ii) a makeup and/or care composition in accordance with the invention placed inside said compartment(s).

The container may be, for example, in the form of a jar or a box.

The closing member may be in the form of a lid comprising a cap mounted so as to be able to move by translation or by pivoting relative to the container housing said makeup and/or care composition(s).

EXAMPLES

The examples which follow serve to illustrate the invention without, however, exhibiting a limiting nature.

Example A1: Preparation of Compound (14)

[formula 14]

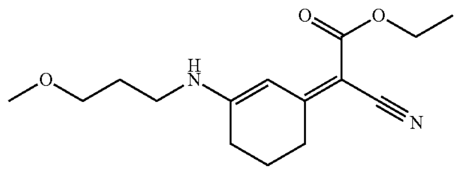

122.23 g of 3-[(3-methoxypropyl)amino]-2-cyclohexen-1-one are alkylated with dimethyl sulfate or alternatively with diethyl sulfate and treated with 75.45 g of ethyl cyanoacetate in approximately equimolar proportions in the presence of a base and optionally of a solvent.

The base/solvent combinations indicated in the following table are used.

TABLE 2

| Example | Base | Solvent |
|---|---|---|
| Example A1.1 | DBU (1,8-diazabicyclo[5.4.0]undec-7-ene) | dimethylacetamide |
| Example A1.2 | triethylamine | isopropanol |
| Example A1.3 | 3-methoxypropylamine | isopropanol |
| Example A1.4 | 3-methoxypropylamine | tert-amyl alcohol |
| Example A1.5 | 3-methoxypropylamine | toluene |
| Example A1.6 | 3-methoxypropylamine | dimethylformamide |
| Example A1.7 | 3-methoxypropylamine | no solvent |
| Example A1.8 | N-morpholine | isopropanol |

The completion of the alkylation reaction can be monitored, for example, by methods such as TLC, GC or HPLC.

162.30 g of compound (14) are obtained in the form of a brown oil.

After crystallization, the product is obtained in the form of yellowish crystals.

Melting point: 92.7° C.

Example A2: Preparation of Compound (15)

[formula 15]

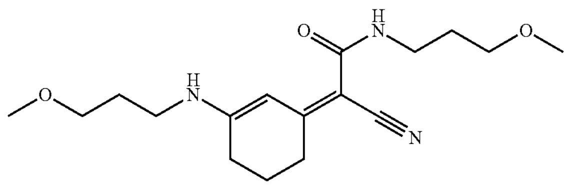

101.00 g of 3-[(3-methoxypropyl)amino]-2-cyclohexen-1-one are alkylated with dimethyl sulfate or alternatively with diethyl sulfate and treated with 86.00 g of 2-cyano-N-(3-methoxypropyl)acetamide in approximately equimolar proportions in the presence of a base and optionally of a solvent.

The base/solvent combinations indicated in the following table are used.

TABLE 3

| Example | Base | Solvent |
|---|---|---|
| Example A2.1 | DBU (1,8-diazabicyclo[5.4.0]undec-7-ene) | dimethylacetamide |
| Example A2.2 | triethylamine | isopropanol |
| Example A2.3 | 3-methoxypropylamine | isopropanol |
| Example A2.4 | 3-methoxypropylamine | tert-amyl alcohol |
| Example A2.5 | 3-methoxypropylamine | toluene |
| Example A2.6 | 3-methoxypropylamine | dimethylformamide |
| Example A2.7 | 3-methoxypropylamine | no solvent |

The crude product (15) is obtained in the form of a dark brown oil.

After silica gel column chromatography (eluent: 99/1 toluene/methanol), 81.8 grams of product are obtained in the form of yellowish crystals.

Melting point: 84.7-85.3° C.

Example A3: Preparation of Compound (27)

[formula 27]

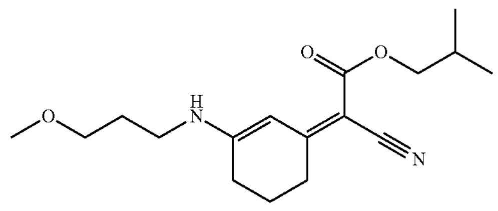

13.09 g of 3-[(3-methoxypropyl)amino]-2-cyclohexen-1-one are alkylated with dimethyl sulfate or alternatively with diethyl sulfate and treated with 10.12 g of isobutyl cyanoacetate in the presence of a base and optionally of a solvent.

The base/solvent combinations indicated in the following table are used.

TABLE 4

| Example | Base | Solvent |
|---|---|---|
| Example A3.1 | DBU (1,8-diazabicyclo[5.4.0]undec-7-ene) | dimethylacetamide |
| Example A3.2 | triethylamine | isopropanol |
| Example A3.3 | 3-methoxypropylamine | isopropanol |
| Example A3.4 | N-methylmorpholine | tert-amyl alcohol |
| Example A3.5 | 3-methoxypropylamine | toluene |
| Example A3.6 | 3-methoxypropylamine | dimethylformamide |
| Example A3.7 | 3-methoxypropylamine | no solvent |

15.97 grams of crude product (27) are obtained in the form of a dark brown oil.

After silica gel column chromatography (eluent: toluene/acetone), 13.46 grams of product are obtained in the form of yellowish crystals.

Melting point: 96.3° C.

Example A4: Preparation of Compound (25)

[formula 25]

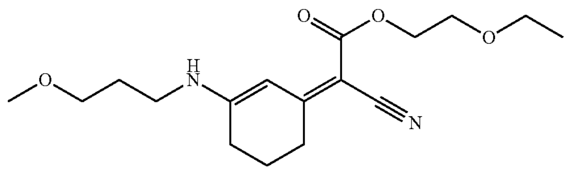

148.4 g of 3-[(3-methoxypropyl)amino]-2-cyclohexen-1-one are alkylated with dimethyl sulfate or alternatively with diethyl sulfate and treated with 130.00 g of 2-ethoxyethyl cyanoacetate in the presence of an organic base and of a solvent.

The base/solvent combinations indicated in the table below are used.

TABLE 5

| Example | Base | Solvent |
|---|---|---|
| Example A4.1 | DBU (1,8-diazabicyclo[5.4.0]undec-7-ene) | dimethylacetamide |
| Example A4.2 | triethylamine | isopropanol |
| Example A4.3 | 3-methoxypropylamine | isopropanol |
| Example A4.4 | N-methylmorpholine | tert-amyl alcohol |
| Example A4.5 | 3-methoxypropylamine | toluene |
| Example A4.6 | 3-methoxypropylamine | dimethylformamide |
| Example A4.7 | 3-methoxypropylamine | no solvent |

Formulation Examples

Solubilization Examples 1 to 7

Protocol for Evaluating Solubility

The solubility of merocyanine in the oily and/or aqueous solutions can be evaluated macroscopically and/or microscopically. It is considered that the merocyanine is soluble if, at ambient temperature, the solution appears to the eye to be clear and translucent, and it does not have any visible crystals under a white-light or polarized-light microscope (objective ×20 to ×40).

In the examples that follow, the solubility is evaluated macroscopically. It is evaluated at ambient temperature, on the day the solution is prepared and then over time. During this time period, the solutions are stored at ambient temperature.

In Examples 1 to 7, the amounts of the composition ingredients are given as % by weight of starting materials, relative to the total weight of the composition.

Comparative Examples 1 and 2: Solubilization in the Presence of Gamma-Valerolactone The following solutions were prepared according to the process above.

TABLE 6

| Ingredients | 1 (outside the invention) | 2 (invention) |
|---|---|---|
| Compound (25) | 20 | 20 |
| Gamma-valerolactone sold by All Organic Treasures GmbH | — | 80 |
| Propylene carbonate sold by Merck KGaA | 80 | — |
| Solubility at $t_0$ | soluble | soluble |
| Solubility at ambient temperature at 24 hours | insoluble | soluble |

Preparation Method

The compositions described in Examples 1 and 2 are prepared in the following manner: mix all the ingredients, heat to around 55° C. and stir regularly by hand until a clear mixture is obtained (1 to 5 minutes). Leave to dry for 12 hours at room temperature. The solubility of the compositions is then observed according to the protocol as defined below.

Comparative Examples 3 and 4: Solubilization in the Presence of 2-Pyrrolidone The following solutions were prepared according to the process below.

TABLE 7

| Ingredients | 3 (outside the invention) | 4 (invention) |
|---|---|---|
| Compound (25) | 20 | 20 |
| 2-pyrrolidone sold by Sigma Aldrich | — | 80 |
| Propylene carbonate sold by Merck KGaA | 80 | — |
| Solubility at $t_0$ | soluble | soluble |
| Solubility at ambient temperature at 24 hours | insoluble | soluble |

Preparation Method

The compositions described in Examples 3 and 4 are prepared in the following manner: mix all the ingredients, heat to around 55° C. and stir regularly by hand until a clear mixture is obtained (1 to 5 minutes). Leave to dry for 12 hours at room temperature. The solubility of the compositions is then observed according to the protocol as defined below.

Comparative Examples 5 and 6: Solubilization in the Presence of 1-butyl-5-oxopyrrolidone-3-carboxylic acid The following solutions were prepared according to the process below.

TABLE 8

| Ingredients | 5 (outside the invention) | 6 (invention) |
|---|---|---|
| Compound (25) | 10 | 10 |
| 1-Butyl-5-oxopyrrolidone-3-carboxylic acid | — | 10 |

TABLE 8-continued

| Ingredients | 5 (outside the invention) | 6 (invention) |
|---|---|---|
| ISOPROPYL LAUROYL SARCOSINATE (ELDEW SL-205 from AJINOMOTO) | 90 | 80 |
| Solubility at $t_0$ | soluble | soluble |
| Solubility at ambient temperature at 48 hours | insoluble | soluble |

Preparation Method

The compositions described in Examples 5 and 6 are prepared in the following manner: mix all the ingredients, heat to around 80° C. and stir with a magnetic stirrer bar until completely dissolved (around 1 hour). The solubility of the compositions is then observed macroscopically while hot (point denoted as t0), after returning to room temperature, and 48 hours after returning to room temperature.

Example 7: Solubilization in the Presence of 1,3-dimethylbutyl 1-butyl-5-oxopyrrolidone-3-carboxylate The following solutions were prepared according to the process below.

TABLE 9

| Ingredients | 7 (invention) |
|---|---|
| Compound (25) | 10 |
| 1,3-dimethylbutyl 1-butyl-5-oxopyrrolidine-3-carboxylate | 90 |
| Solubility at $t_0$ | soluble |
| Solubility at ambient temperature at 24 hours | soluble |

Preparation Method

The various raw materials are successively introduced into a container before being mixed using a magnetic stirrer and being heated to 80° C. to 90° C. for 1 hour, until all the compounds are solubilized.

The mixture is then then left to stand in order to return to ambient temperature, at which it is kept.

Examples 8 to 10: Solubilization in the Presence of PCA and PCA Ester

The following solutions were prepared according to the process below.

TABLE 10

| Ingredients | 8 (outside the invention) | 9 (invention) | 10 (invention) |
|---|---|---|---|
| Compound 25 | 50 mg | 50 mg | 50 mg |
| 2-pyrrolidone 5-carboxylic acid (PCA) Sigma Aldrich | — | 20 mg | — |
| Butyl (S)-2-pyrrolidone 5-carboxylate (PCA ester) Sigma Aldrich | — | — | 29 mg |

TABLE 10-continued

| Ingredients | 8 (outside the invention) | 9 (invention) | 10 (invention) |
|---|---|---|---|
| Water buffered at pH 5 with citric acid | 5 g | 5 g | 5 g |
| pH measured | 5 | 2.5 | 3.2 |
| Absorption at 385 nm | 0.66 | 0.78 | 1.17 |

Procedure and Evaluation of Solubility

Mix all the ingredients and leave under mechanical stirring for 24 hours at ambient temperature.

Filter the mixture using a 0.2 μm diameter PTFE is syringe filter in order to extract a clear liquid.

Remove 30 μl of the liquid and dilute it in 5 ml of ethanol.

Introduce the diluted solution into a 1 cm cuvette and run a UV/Visible spectrum of the solution.

Apparatus: Perkin Elmer Lambda 19 spectrophotometer.

Results

The results obtained show that the gamma-butyrolactones of the invention such as PCA and the PCA ester make it possible to solubilise a greater amount of merocyanine in water.

The invention claimed is:

1. A cosmetic or dermatological composition comprising:

a) at least one merocyanine corresponding to formula (3) below, and also the geometric isomer forms thereof:

[formula 3]

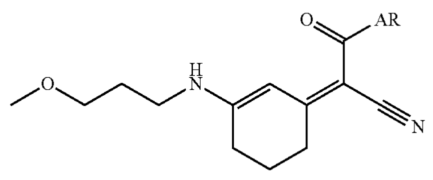

in which:

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, it being possible for said groups to be interrupted by one or more O; and b) at least one compound chosen from gamma-butyrolactones and gamma-butyrolactams of the formula as defined below, and also the organic or mineral acid or base salts thereof, and the solvates thereof:

[formula 38]

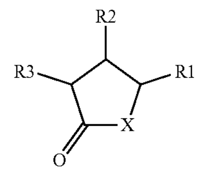

in which:

X represents an oxygen atom, a sulfur atom or a nitrogen atom bearing an R4 radical, with R4 representing a hydrogen atom or a linear or branched $C_1$-$C_6$, R1, R2 and R3 represent, independently of one another:

a hydrogen atom, a linear or branched $C_1$-$C_6$ alkyl radical, or an —$[O]_n$—C(O)—$[O]_p$—R5 radical, where:

n is equal to 0 or 1, p is equal to 0 or 1, with n+p equal to 1 or 2,

R5 represents a hydrogen atom or a linear or branched $C_1$-$C_6$ alkyl radical.

2. The cosmetic or dermatological composition according to claim 1, in which the weight ratio of the total amount of compounds chosen from gamma-butyrolactones and gamma-butyrolactams of formula (38) to the total amount of merocyanines of formula (3) is greater than or equal to 0.2/1.

3. The cosmetic or dermatological composition according to claim 1, in which the weight ratio of the total amount of compounds chosen from gamma-butyrolactones and gamma-butyrolactams of formula (38) to the total amount of merocyanines of formula (3) is less than or equal to 50/1.

4. The cosmetic or dermatological composition according to claim 1, wherein the merocyanines of formula (3) are chosen from the following compounds, and also the geometric isomer forms thereof:

compound 14

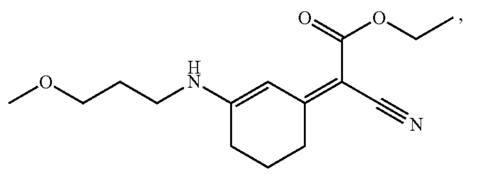 [SMILES: CCOC(=O)/C(C#N)=C1\C=C(NCCCOC)CCC1]

ethyl (2Z)-cyano {3-[(3-methoxypropyl)amino]cyclohex-2-en-1-ylidene}ethanoate;

compound 15

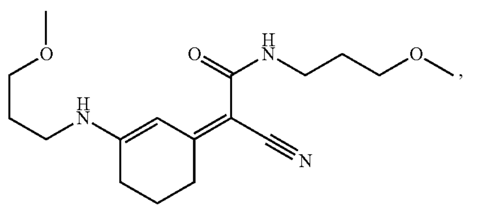 [SMILES: COCCCNC(=O)/C(C#N)=C1\C=C(NCCCOC)CCC1]

(2Z)-2-cyano-N-(3-methoxypropyl)-2-{3-[(3-methoxypropyl)amino]cyclohex-2-en-1-ylidene}ethanamide;

compound 25

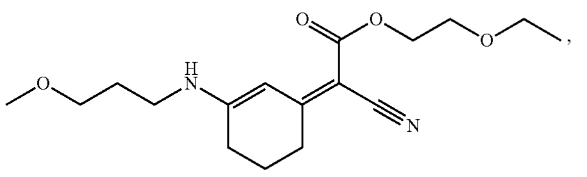 [SMILES: CCOCCOC(=O)/C(C#N)=C1\C=C(NCCCOC)CCC1]

2-ethoxyethyl (2Z)-cyano {3-[(3-methoxypropyl)amino]cyclohex-2-en-1-ylidene}ethanoate;

compound 27

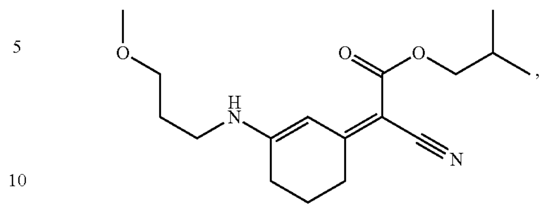

2-methylpropyl (2Z)-cyano {3-[(3-methoxypropyl)amino]cyclohex-2-en-1-ylidene}ethanoate;

compound 29

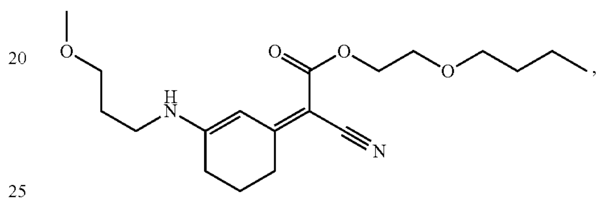

2-butoxyethyl (2Z)-cyano {3-[(3-methoxypropyl)amino]cyclohex-2-en-1-ylidene}ethanoate;

compound 31

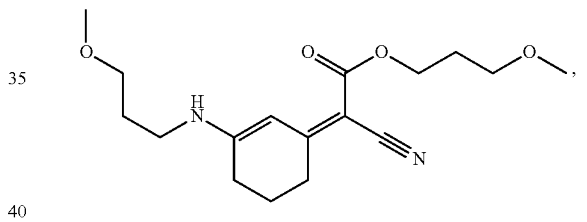

3-methoxypropyl (2Z)-cyano {3-[(3-methoxypropyl)amino]cyclohex-2-en-1-ylidene}ethanoate and compound 37

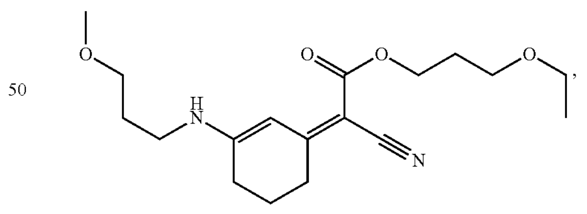

3-ethoxypropyl (2Z)-cyano {3-[(3-methoxypropyl)amino]cyclohex-2-en-1-ylidene}ethanoate.

5. The cosmetic or dermatological composition according to claim 1, in which the merocyanine of formula (3) is 2-ethoxyethyl (2Z)-cyano {3-[(3-methoxypropyl)amino]cyclohex-2-en-1-ylidene}ethanoate (25) in its E/Z geometric configuration having the following structure:

[formula 25]

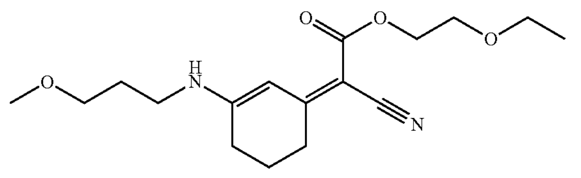

and/or in its E/E geometric configuration having the following structure:

[formula 25a]

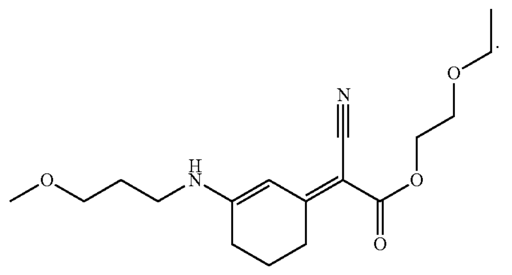

6. The cosmetic or dermatological composition according to claim 1, in which, in formula 38, R1, R2, R3 represent, independently of one another:

a hydrogen atom, a linear or branched $C_1$-$C_6$ alkyl radical, or an —$[O]_n$—C(O)—$[O]_p$—R5 radical, where:

n is equal to 0 or 1, p is equal to 0 or 1, with n+p equal to 1,

R5 represents a hydrogen atom or a linear or branched $C_1$-$C_6$ alkyl radical.

7. The cosmetic or dermatological composition according to claim 1, in which, in formula 38, n=1 and p=0.

8. The cosmetic or dermatological composition according to claim 1, comprising at least one gamma-butyrolactone in which X is an oxygen atom.

9. The cosmetic or dermatological composition according to claim 1, comprising at least one gamma-butyrolactam in which X is a nitrogen atom bearing an R4 radical.

10. The cosmetic or dermatological composition according to claim 1, comprising at least one compound chosen from gamma-valerolactone, 2-pyrrolidone, 1,3-dimethylbutyl 1-butyl-5-oxopyrrolidine-3-carboxylate, 2-pyrrolidone-5-carboxylic acid (PCA), tert-butyl(S)-2-pyrrolidone-5-carboxylate (PCA ester) and 1-butyl-5-oxopyrrolidone-3-carboxylic acid.

11. The cosmetic or dermatological composition according to claim 1, further comprising one or more additional UV-screening agents.

12. A non-therapeutic cosmetic method for caring for and/or making up a keratin material, comprising the application, to the surface of said keratin material, of at least one composition as defined according to claim 1.

13. The cosmetic or dermatological composition according to claim 2, in which the weight ratio of the total amount of compounds chosen from gamma-butyrolactones and gamma-butyrolactams of formula (38) to the total amount of merocyanines of formula (3) is less than or equal to 50/1.

14. The cosmetic or dermatological composition according to claim 2, wherein the merocyanines of formula (3) are chosen from the following compounds, and also the geometric isomer forms thereof:

compound 14

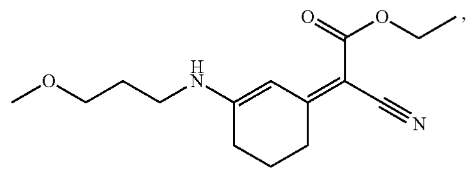 [SMILES: CCOC(=O)/C(C#N)=C1\C=C(NCCCOC)CCC1]

ethyl (2Z)-cyano {3-[(3-methoxypropyl)amino]cyclohex-2-en-1-ylidene}ethanoate;

compound 15

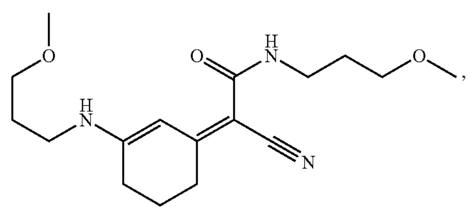 [SMILES: COCCCNC(=O)/C(C#N)=C1\C=C(NCCCOC)CCC1]

(2Z)-2-cyano-N-(3-methoxypropyl)-2-{3-[(3-methoxypropyl)amino]cyclohex-2-en-1-ylidene}ethanamide;

compound 25

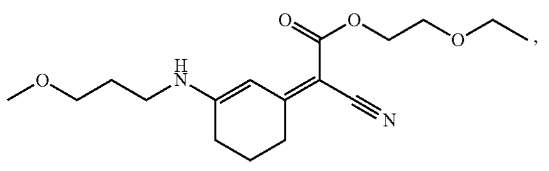 [SMILES: CCOCCOC(=O)/C(C#N)=C1\C=C(NCCCOC)CCC1]

2-ethoxyethyl (2Z)-cyano {3-[(3-methoxypropyl)amino]cyclohex-2-en-1-ylidene}ethanoate;

compound 27

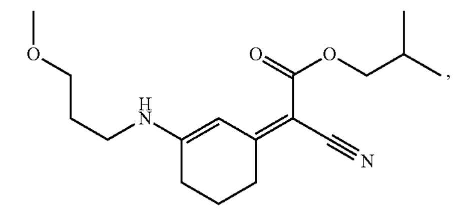 [SMILES: COCCCNC1=C/C(=C(/C#N)C(=O)OCC(C)C)CCC1]

2-methylpropyl (2Z)-cyano {3-[(3-methoxypropyl)amino]cyclohex-2-en-1-ylidene}ethanoate;

compound 29

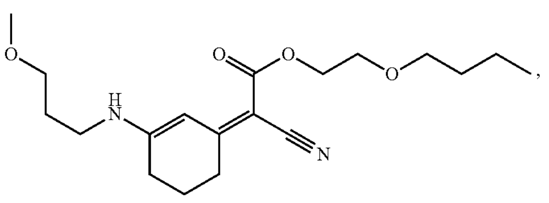 [SMILES: CCCCOCCOC(=O)/C(C#N)=C1\C=C(NCCCOC)CCC1]

2-butoxyethyl (2Z)-cyano {3-[(3-methoxypropyl)amino]cyclohex-2-en-1-ylidene}ethanoate;

compound 31

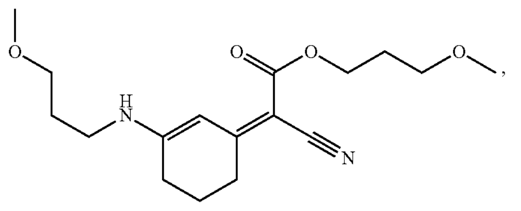 [SMILES: COCCCNC1=C/C(=C(/C#N)C(=O)OCCCOC)CCC1]

3-methoxypropyl (2Z)-cyano {3-[(3-methoxypropyl) amino]cyclohex-2-en-1-ylidene}ethanoate and compound 37

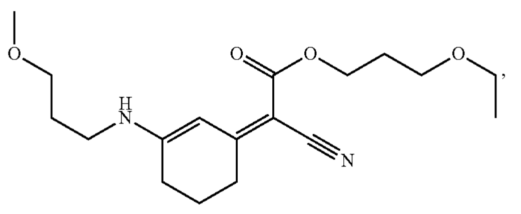 [SMILES: CCOCCCOC(=O)/C(C#N)=C1\C=C(NCCCOC)CCC1]

3-ethoxypropyl (2Z)-cyano {3-[(3-methoxypropyl)amino] cyclohex-2-en-1-ylidene}ethanoate.

15. The cosmetic or dermatological composition according to claim 3, wherein the merocyanines of formula (3) are chosen from the following compounds, and also the geometric isomer forms thereof:

compound 14

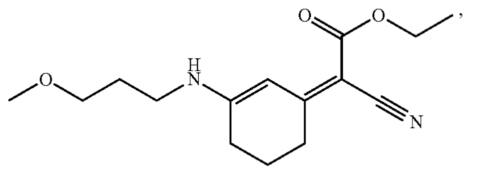 [SMILES: CCOC(=O)/C(C#N)=C1\C=C(NCCCOC)CCC1]

ethyl (2Z)-cyano {3-[(3-methoxypropyl)amino]cyclohex-2-en-1-ylidene}ethanoate;

compound 15

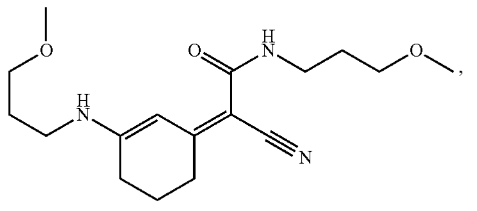 [SMILES: COCCCNC(=O)/C(C#N)=C1\C=C(NCCCOC)CCC1]

(2Z)-2-cyano-N-(3-methoxypropyl)-2-{3-[(3-methoxypropyl)amino]cyclohex-2-en-1-ylidene}ethanamide;

compound 25

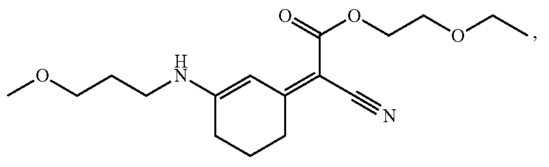 [SMILES: CCOCCOC(=O)/C(C#N)=C1\C=C(NCCCOC)CCC1]

2-ethoxyethyl (2Z)-cyano {3-[(3-compound 25-methoxypropyl)amino]cyclohex-2-en-1-ylidene}ethanoate;

compound 27

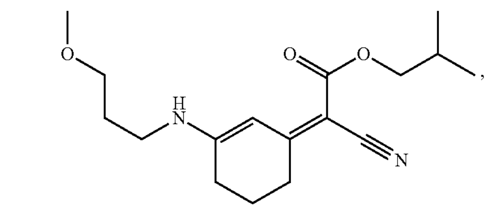 [SMILES: COCCCNC1=C/C(=C(/C#N)C(=O)OCC(C)C)CCC1]

2-methylpropyl (2Z)-cyano {3-[(3-methoxypropyl) amino]cyclohex-2-en-1-ylidene}ethanoate;

compound 29

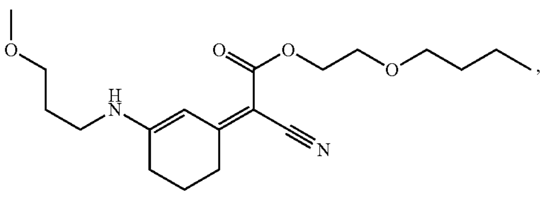 [SMILES: CCCCOCCOC(=O)/C(C#N)=C1\C=C(NCCCOC)CCC1]

2-butoxyethyl (2Z)-cyano {3-[(3-methoxypropyl) amino]cyclohex-2-en-1-ylidene}ethanoate;

compound 31

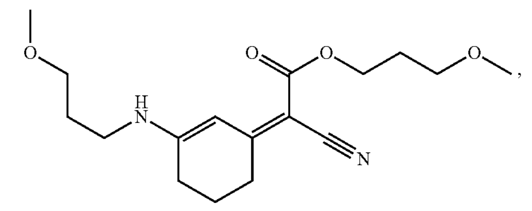 [SMILES: COCCCNC1=C/C(=C(/C#N)C(=O)OCCCOC)CCC1]

3-methoxypropyl (2Z)-cyano {3-[(3-methoxypropyl) amino]cyclohex-2-en-1-ylidene}ethanoate and compound 37

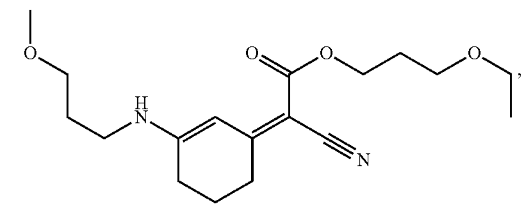 [SMILES: CCOCCCOC(=O)/C(C#N)=C1\C=C(NCCCOC)CCC1]

3-ethoxypropyl (2Z)-cyano {3-[(3-methoxypropyl)amino] cyclohex-2-en-1-ylidene}ethanoate.

16. The cosmetic or dermatological composition according to claim 2, in which the merocyanine of formula (3) is 2-ethoxyethyl (2Z)-cyano {3-[(3-methoxypropyl)amino]cyclohex-2-en-1-ylidene}ethanoate (25) in its E/Z geometric configuration having the following structure:

[formula 25]

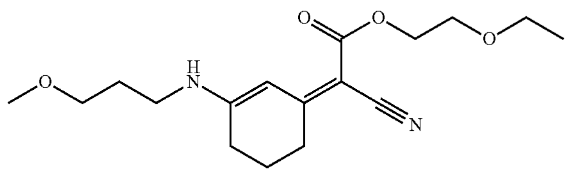

and/or in its E/E geometric configuration having the following structure:

[formula 25a]

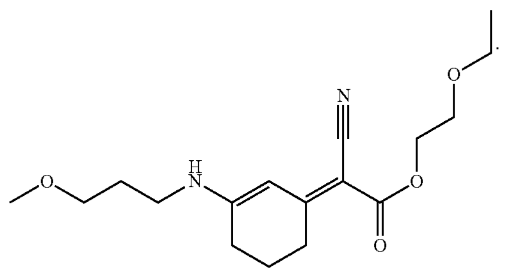

17. The cosmetic or dermatological composition according to claim 3, in which the merocyanine of formula (3) is 2-ethoxyethyl (2Z)-cyano {3-[(3-methoxypropyl)amino]cyclohex-2-en-1-ylidene}ethanoate (25) in its E/Z geometric configuration having the following structure:

[formula 25]

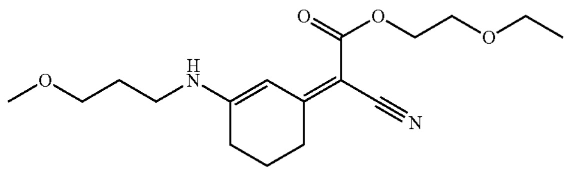

and/or in its E/E geometric configuration having the following structure:

[formula 25a]

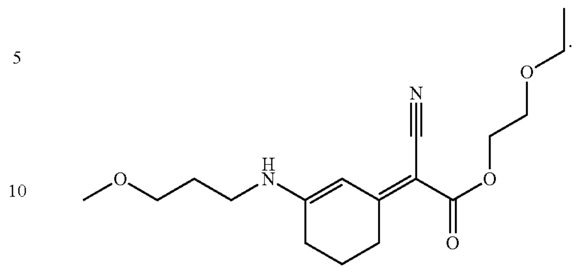

18. The cosmetic or dermatological composition according to claim 4, in which the merocyanine of formula (3) is 2-ethoxyethyl (2Z)-cyano {3-[(3-methoxypropyl)amino]cyclohex-2-en-1-ylidene}ethanoate (25) in its E/Z geometric configuration having the following structure:

[formula 25]

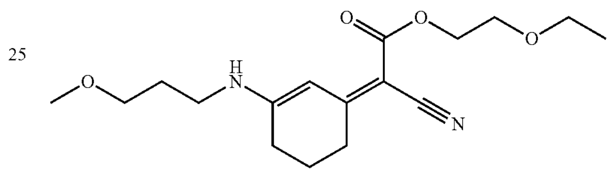

and/or in its E/E geometric configuration having the following structure:

[formula 25a]

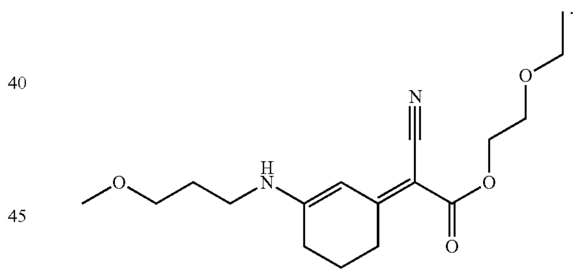

19. The cosmetic or dermatological composition according to claim 2, in which, in formula 38, R1, R2, R3 represent, independently of one another:

a hydrogen atom, a linear or branched $C_1$-$C_6$, alkyl radical, or an —$[O]_n$—C(O)—$[O]_p$—R5 radical, where:

n is equal to 0 or 1, p is equal to 0 or 1, with n+p equal to 1,

R5 represents a hydrogen atom or a linear or branched $C_1$-$C_6$ alkyl radical.

20. A method for solubilizing a merocyanine corresponding to the following formula (3) and also their geometrical isomer forms:

[Formula 3]

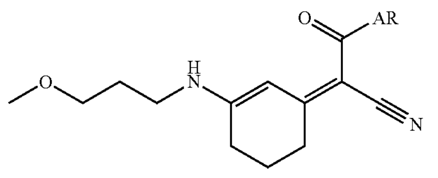

in which:

A is —O— or —NH—;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, it being possible for said groups to be interrupted by one or more O in the fatty phase and/or in the aqueous phase of a composition, which comprises including in the composition at least one compound chosen from gamma-butyrolactones and gamma-butyrolactams of the formula as defined below, and also the organic or mineral acid or base salts thereof, and the solvates thereof such as hydrates:

[formula 38]

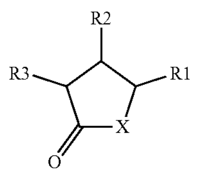

in which:

X represents an oxygen atom, a sulfur atom or a nitrogen atom bearing an R4 radical, with R4 representing a hydrogen atom or a linear or branched $C_1$-$C_6$, R1, R2 and R3 represent, independently of one another:

a hydrogen atom, a linear or branched $C_1$-$C_6$ alkyl radical, or an $—[O]_n—C(O)—[O]_p—$R5 radical, where:

n is equal to 0 or 1, p is equal to 0 or 1, with n+p equal to 1 or 2,

R5 represents a hydrogen atom or a linear or branched $C_1$-$C_6$ alkyl radical.

21. The cosmetic or dermatological composition according to claim 1, in which the weight ratio of the total amount of compounds chosen from gamma-butyrolactones and gamma-butyrolactams of formula (38) to the total amount of merocyanines of formula (3) is greater than or equal to 10/1 and less than or equal to 20/1, the total amount of the merocyanines of formula (3) ranges from 0.1% to 15% by weight relative to the total weight of the composition.

22. The cosmetic or dermatological composition according to claim 21, comprising at least one compound chosen from gamma-valerolactone, 2-pyrrolidone, 1,3-dimethylbutyl 1-butyl-5-oxopyrrolidine-3-carboxylate, 2-pyrrolidone-5-carboxylic acid (PCA), tert-butyl(S)-2-pyrrolidone-5-carboxylate (PCA ester) and 1-butyl-5-oxopyrrolidone-3-carboxylic acid; and The cosmetic or dermatological composition according to claim 2, wherein the merocyanines of formula (3) are chosen from the following compounds, and also the geometric isomer forms thereof:

compound 14

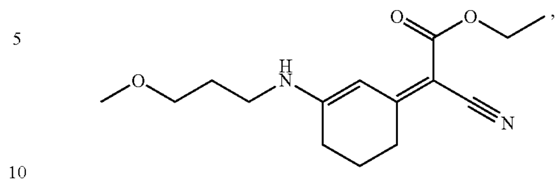

ethyl (2Z)-cyano {3-[(3-methoxypropyl)amino]cyclohex-2-en-1-ylidene}ethanoate;

compound 15

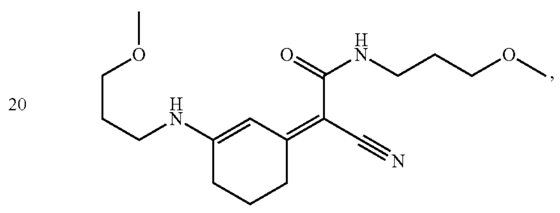

(2Z)-2-cyano-N-(3-methoxypropyl)-2-{3-[(3-methoxypropyl)amino]cyclohex-2-en-1-ylidene}ethanamide;

compound 25

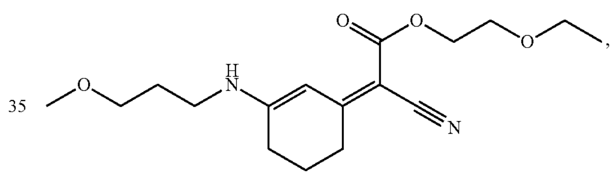

2-ethoxyethyl (2Z)-cyano {3-[(3-methoxypropyl)amino] cyclohex-2-en-1-ylidene}ethanoate;

compound 27

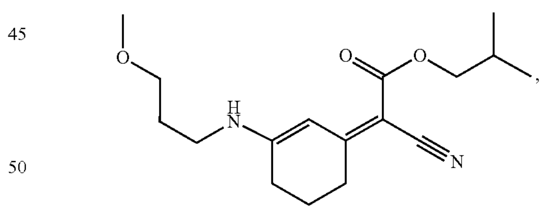

2-methylpropyl (2Z)-cyano {3-[(3-methoxypropyl) amino]cyclohex-2-en-1-ylidene}ethanoate;

compound 29

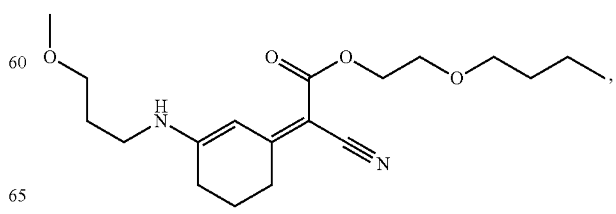

2-butoxyethyl (2Z)-cyano {3-[(3-methoxypropyl) amino]cyclohex-2-en-1-ylidene}ethanoate;

compound 31

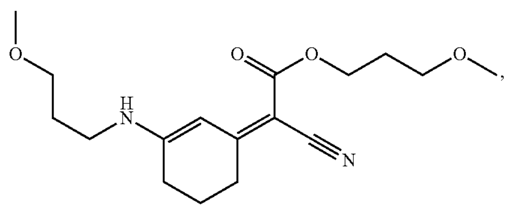 [SMILES: COCCCNC1=C/C(=C(/C#N)C(=O)OCCCOC)CCC1]

3-methoxypropyl (2Z)-cyano {3-[(3-methoxypropyl) amino]cyclohex-2-en-1-ylidene}ethanoate and compound 37

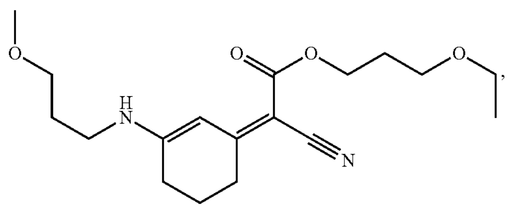 [SMILES: CCOCCCOC(=O)/C(C#N)=C1\C=C(NCCCOC)CCC1]

3-ethoxypropyl (2Z)-cyano {3-[(3-methoxypropyl) amino]cyclohex-2-en-1-ylidene}ethanoate.

23. The cosmetic or dermatological composition according to claim 22, in which the merocyanine of formula (3) is 2-ethoxyethyl (2Z)-cyano {3-[(3-methoxypropyl)amino]cyclohex-2-en-1-ylidene}ethanoate (25) in its E/Z geometric configuration having the following structure:

[formula 25]

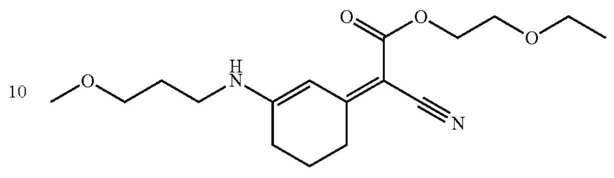

and/or in its E/E geometric configuration having the following structure:

[formula 25a]

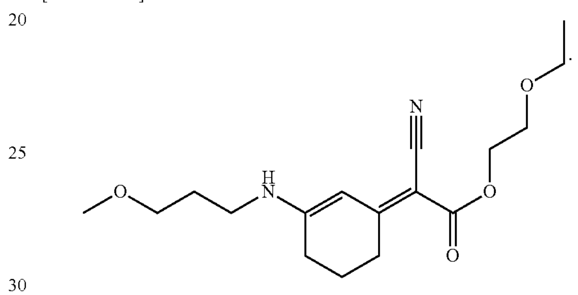

* * * * *